United States Patent
Luberski et al.

(10) Patent No.: US 10,104,901 B2
(45) Date of Patent: *Oct. 23, 2018

(54) OPTIMIZING EGG PRODUCTION CHARACTERISTICS VIA SEAWATER MINERALIZATION

(71) Applicant: Luberski Inc., Fullerton, CA (US)

(72) Inventors: Timothy E. Luberski, Fullerton, CA (US); Neal Rye, Perris, CA (US); Edward E. Anderson, Yorba Linda, CA (US)

(73) Assignee: Luberski, Inc., Fullerton, CA (US)

( * ) Notice: Subject to any disclaimer, the term of this patent is extended or adjusted under 35 U.S.C. 154(b) by 921 days.

This patent is subject to a terminal disclaimer.

(21) Appl. No.: 14/088,182

(22) Filed: Nov. 22, 2013

(65) Prior Publication Data

US 2014/0079803 A1  Mar. 20, 2014

Related U.S. Application Data

(63) Continuation-in-part of application No. 13/449,213, filed on Apr. 17, 2012.

(51) Int. Cl.
  *A01K 45/00* (2006.01)
  *A23K 1/18* (2006.01)
  (Continued)

(52) U.S. Cl.
  CPC ............ *A23K 1/1826* (2013.01); *A01K 43/00* (2013.01); *A01K 45/00* (2013.01); *A01K 45/007* (2013.01);
  (Continued)

(58) Field of Classification Search
  USPC .......................................................... 119/6.8
  See application file for complete search history.

(56) References Cited

U.S. PATENT DOCUMENTS

2005/0281918 A1* 12/2005 Shibata et al. ................. 426/72
2009/0061016 A1*  3/2009 Selzer et al. ................. 424/600
(Continued)

FOREIGN PATENT DOCUMENTS

EP         1161886 A1 * 12/2001 ............... A23L 2/38
JP       2010-88311    *  4/2010 ............. A23K 1/175
(Continued)

OTHER PUBLICATIONS

Calcium Supplementation of Hen Drinking Water, Poultry Science (1995) 74 (5):784-787, by B.L. Damron and L.K. Flunker,1 page, http://ps.oxfordjournals.org/content/74/4/784.abstract [retrieved from internet on Apr. 20, 2016.*
(Continued)

*Primary Examiner* — Andrea M Valenti
(74) *Attorney, Agent, or Firm* — Gibb & Riley, LLC

(57) ABSTRACT

Aspects for utilizing a seawater fluid to optimize egg-production characteristics are disclosed. In one aspect, a method is provided, which includes identifying a desired optimization, determining a corresponding seawater to non-seawater ratio, and generating a seawater fluid according to the ratio. An egg-cultivation method is also provided, which includes ascertaining a desired optimization, selecting a corresponding seawater to non-seawater ratio, and providing a seawater fluid comprising the ratio to a hen. In another egg-cultivation method, hens are provided with a mixed feed comprising a feed to seawater-mineralized produce ratio selected according to a desired optimization. A method to grow produce is also provided, which includes mineralizing soil with a seawater fluid comprising a seawater to non-seawater ratio corresponding to a preferred optimization. In another aspect, a method to produce feed is disclosed, which includes mixing feed with mineralized produce according to a ratio corresponding to a desired optimization.

20 Claims, 21 Drawing Sheets

(51) Int. Cl.
| | |
|---|---|
| C02F 1/44 | (2006.01) |
| C02F 1/52 | (2006.01) |
| C02F 1/14 | (2006.01) |
| C02F 1/461 | (2006.01) |
| A61K 35/08 | (2015.01) |
| A01K 43/00 | (2006.01) |
| A23K 20/189 | (2016.01) |
| A23K 20/20 | (2016.01) |
| A23K 20/22 | (2016.01) |
| A23K 20/24 | (2016.01) |
| A23K 50/75 | (2016.01) |

(52) U.S. Cl.
CPC ............ *A23K 20/189* (2016.05); *A23K 20/20* (2016.05); *A23K 20/22* (2016.05); *A23K 20/24* (2016.05); *A23K 20/30* (2016.05); *A23K 50/75* (2016.05); *A61K 35/08* (2013.01); *C02F 1/14* (2013.01); *C02F 1/441* (2013.01); *C02F 1/461* (2013.01); *C02F 1/52* (2013.01)

(56) References Cited

U.S. PATENT DOCUMENTS

2009/0061050 A1* 3/2009 Selzer et al. .................... 426/72
2011/0010154 A1* 1/2011 Cook et al. ...................... 703/11
2015/0104424 A1* 4/2015 Scivoletto et al. .......... 424/93.4

FOREIGN PATENT DOCUMENTS

| KR | 2010Q51411 | * 10/2010 | ............... A23K 1/16 |
| KR | 2012049500 A | * 5/2012 | ............. A23K 1/175 |

OTHER PUBLICATIONS

English Translation of Japanese Patent to Ogura JP 2010-088311A; entitled JP English Ogura claims, drawings, detailed description.*
Office Action Communication, U.S. Appl. No. 13/449,213, dated Jan. 20, 2015, pp. 1-10.
Office Action Communication, U.S. Appl. No. 13/449,213, dated Sep. 16, 2014, pp. 1-7.
U.S. Appl. No. 13/449,213, Office Action Communication dated Aug. 18, 2016, 18 Pages.
U.S. Appl. No. 13/449,213, Office Action Communication dated Nov. 1, 2016, 3 Pages.
U.S. Appl. No. 13/449,213, Examiner's Answer dated Apr. 3, 2017, 10 Pages.

* cited by examiner

OPTIMIZING EGG PRODUCTION CHARACTERISTICS VIA SEAWATER MINERALIZATION

CROSS-REFERENCE TO RELATED APPLICATIONS

This application is a continuation-in-part of U.S. patent application Ser. No. 13/449,213, filed Apr. 17, 2012, entitled "OPTIMIZING EGG PRODUCTION CHARACTERISTICS VIA SEAWATER MINERALIZATION," which is incorporated herein by reference in its entirety.

TECHNICAL FIELD

The subject disclosure generally relates to optimizing egg-production characteristics, and more specifically to optimizing such characteristics by providing chickens with produce and water mineralized with a seawater fluid.

BACKGROUND

By way of background concerning conventional feeding methods, it is noted that such methods are limited with respect to optimizing particularly desirable egg production characteristics. For instance, it is desirable to farm robust eggs that will not crack while being transported to the marketplace. Producing eggs that are larger, and with particular consumption characteristics (e.g., flavor, calories, cholesterol, etc.), is also desirable. However, despite there being a great demand for eggs that exhibit these and other desirable characteristics, current egg production methods fail to provide an adequate mechanism for efficiently producing such eggs.

Accordingly, it would be desirable to design a chicken feed methodology which overcomes these limitations. To this end, it should be noted that the above-described deficiencies are merely intended to provide an overview of some of the problems of conventional systems, and are not intended to be exhaustive. Other problems with the state of the art and corresponding benefits of some of the various non-limiting embodiments may become further apparent upon review of the following detailed description.

SUMMARY

A simplified summary is provided herein to help enable a basic or general understanding of various aspects of exemplary, non-limiting embodiments that follow in the more detailed description and the accompanying drawings. This summary is not intended, however, as an extensive or exhaustive overview. Instead, the sole purpose of this summary is to present some concepts related to some exemplary non-limiting embodiments in a simplified form as a prelude to the more detailed description of the various embodiments that follow.

In accordance with one or more embodiments and corresponding disclosure, various non-limiting aspects are described in connection with utilizing a seawater solution to optimize egg production characteristics. In one such aspect, a method is provided which includes identifying at least one desired egg production optimization. This method further includes determining a customized ratio of seawater to non-seawater fluid corresponding to the at least one desired egg production optimization. A seawater fluid is then generated, which comprises a quantity of seawater and a quantity of non-seawater fluid according to the customized ratio.

In another aspect, a method to cultivate eggs is provided, which includes ascertaining at least one desired egg production optimization. The method further includes selecting a customized ratio of seawater to non-seawater fluid corresponding to the at least one desired egg production optimization. A seawater fluid is then provided to at least one hen, whereby the seawater fluid comprises a quantity of seawater and a quantity of non-seawater fluid according to the customized ratio.

In a further aspect, a method to grow produce is provided, which includes identifying at least one preferred egg production optimization, and determining a customized ratio of seawater to non-seawater fluid. For this particular embodiment, the customized ratio is a ratio of seawater to non-seawater fluid customized according to the at least one preferred egg production optimization. The method further includes mineralizing a plot of soil with a seawater fluid that comprises a quantity of seawater and a quantity of non-seawater fluid according to the customized ratio. Produce is then grown on the plot of soil.

A method to produce chicken feed is also provided. Within such embodiment, the method includes identifying at least one desired egg production optimization, and ascertaining a customized ratio of feed to mineralized produce corresponding to the at least one desired egg production optimization. Here, mineralized produce is defined as produce grown on soil treated with a seawater fluid. Once the customized ratio is ascertained, the method then concludes by mixing a quantity of feed with a quantity of mineralized produce according to the customized ratio.

In a further aspect, yet another method to cultivate eggs is provided. This method includes ascertaining a desired egg production optimization, and selecting a mixed feed that comprises a ratio of chicken feed to mineralized produce according to the desired egg production optimization. The mixed feed is then provided to at least one hen. Here, mineralized produce is again defined as produce grown on soil treated with a seawater fluid.

In another aspect, a method that facilitates optimizing egg production characteristics is provided. The method includes ascertaining at least one desired hen health optimization, and selecting a customized ratio of seawater to non-seawater fluid corresponding to the desired hen health optimization. The method further includes providing a seawater fluid to at least one hen, in which the seawater fluid comprises a quantity of seawater and a quantity of non-seawater fluid according to the customized ratio.

In a further aspect, another method that facilitates optimizing egg production characteristics is provided. The method includes identifying at least one desired egg production optimization, and ascertaining a desired content of a seawater concentrate corresponding to the desired egg production optimization. The method further includes deriving the seawater concentrate from a seawater sample to include the desired content.

In another aspect, yet another method that facilitates optimizing egg production characteristics is provided. The method includes selecting a seawater concentrate configured to facilitate at least one desired egg production optimization. The method further includes preserving a desired content of the seawater concentrate via a handling protocol, in which the desired content corresponds to the desired egg production optimization.

Other embodiments and various non-limiting examples, scenarios, and implementations are described in more detail below.

BRIEF DESCRIPTION OF THE DRAWINGS

Various non-limiting embodiments are further described with reference to the accompanying drawings in which.

DETAILED DESCRIPTION

Overview

Figure 1:
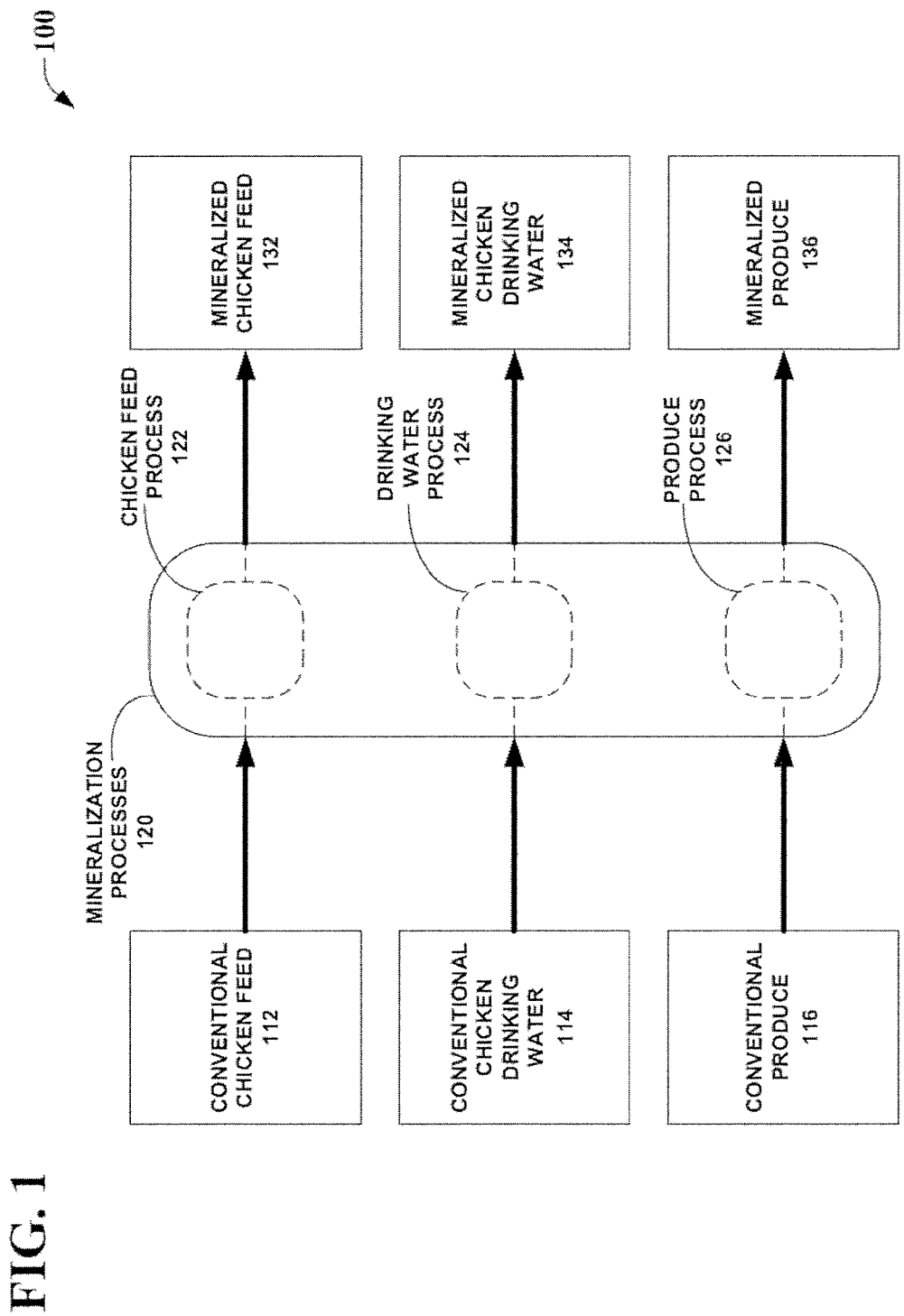
FIG. 1 illustrates a block diagram of exemplary processes for utilizing a seawater fluid according to an embodiment.

As discussed in the background, it is desirable to optimize various characteristics of eggs farmed via conventional chicken feeding methodologies. The various embodiments disclosed herein are directed towards utilizing mineralized produce/water to optimize egg-production characteristics. Namely, it has been discovered that various egg-production characteristics can be desirably optimized by integrating a seawater fluid into a hen's drinking water. It has been further discovered that egg-production characteristics are also optimized by feeding hens a mixture of conventional chicken feed and produce grown on soil mineralized with seawater.

It should be appreciated that "egg-production optimizations", as used herein, are directed towards any of a plurality of characteristics generally known in the egg farming industry as being particularly desirable. For instance, as stated previously, it is desirable to farm robust eggs that will not crack while being transported to the marketplace. Indeed, an exemplary egg-production optimization achieved via the processes disclosed herein is directed towards producing eggs with stronger shells. Producing eggs that are larger, and with particular consumption characteristics (e.g., flavor, calories, cholesterol, etc.) are also desirable, so egg-production optimizations may be directed toward optimizing these characteristics as well.

With respect to producing more robust eggs, it is contemplated that the aspects disclosed herein can be implemented to facilitate increasing egg shell thickness. Namely, because egg shell strength is positively correlated to egg shell thickness, improving egg shell thickness and strength is desirable in order to minimize the economic loss of egg breakage while in transit. In an exemplary trial, shell thickness was measured on seventy-two eggs that were laid by hens that were not given seawater fluid, wherein these eggs were chosen as a control group representing eggs that would typically be found in a grocery store. Shell thickness was also measured on one hundred twenty eggs laid by hens that received a daily dosage of seawater fluid, wherein these hens comprised four separate test flocks. Here, the average shell thickness of the eggs laid by hens that were not given seawater fluid was 0.0094 inches, whereas the average shell thickness of the eggs laid by hens that were dosed with the seawater fluid was 0.0147 inches. Accordingly, by dosing hens with seawater fluid according to the aspects disclosed herein, a 56.3% increase in shell thickness was observed from this particular trial.

Chicken health is also very important in the egg farming industry. Therefore, it should be appreciated that "egg-production optimizations", as used herein, also include any of various desired hen health optimizations directed towards optimizing any of a plurality of bird health related characteristics. Through many trials, the various aspects disclosed herein have been discovered to provide a plurality of hen health related optimizations including, for example, an increased egg count output, a decreased mortality rate, an increased bone strength, and a decreased feed requirement. Results from three exemplary trials for each of these hen health optimizations are provided below, wherein the three trials included a cage-free trial (Trial A), a first caged trial (Trial B), and a second caged trial (Trial C). In trial A, a sample population of 38,605 hens was used which included a control flock of 12,925 hens which did not receive seawater fluid and two test flock populations which did receive seawater fluid comprised of 12,888 hens and 12,792 hens. In trial B, 103,495 hens were used which included a control flock of 66,570 hens that did not receive seawater fluid and a test flock of 36,925 hens that did receive seawater fluid. In trial C, 89,611 hens were used which included a control flock of 47,949 hens that did not receive seawater fluid and a test flock of 41,662 hens that did receive seawater fluid. With regards to observations noted in these trials, it should be appreciated that different egg producers will realize different results dependent upon practices and breed. Nevertheless, the observations noted in these trials illustrate how hen health related optimizations can be achieved via implementation of the seawater mineralization aspects disclosed herein.

With respect to leg bone strength, it is first noted that hens die throughout the laying cycle due to a variety of reasons including natural causes. It is typical for deceased hens to be evaluated to determine cause of death. During this process it is common to perform a leg break test to observe how the leg bone breaks. Namely, because calcium content in hen bones, especially leg bones, is the primary source of calcium that the (laying) hen draws upon to form egg shells, the leg break test provides a quick way to evaluate a hen's ongoing ability to produce eggs with acceptable shell quality. Bones with less calcium are observed to "shatter" when sufficient force is applied to break the bone. Bones with higher levels of calcium are observed to break or fracture cleanly. It is typical for leg bones to be comprised of less calcium as hens age. Hens that drank the seawater fluid described herein exhibited higher levels of leg bone calcium later in the laying cycle than hens that did not ingest seawater fluid.

With respect to egg count output, it is noted that the total egg production for a flock, expressed as dozen eggs produced per starting hen ((total eggs produced/twelve)/number of starting hens in flock) is a commonly used productivity metric used in the egg production industry. It is desirable to maximize egg production per hen. Here, in trial A, dozen eggs per hen increased by an average of 9.32% across the two trial flocks as compared to the control flock. In trial B, dozen eggs produced per starting hens increased 1.3%, and in trial C, dozen eggs produced per starting hens increased by 8.47%.

With respect to feed requirement, it is noted that total pounds of feed consumed by a flock divided by total dozen eggs produced by the flock is another common productivity metric used in the egg producing industry. It is desirable to minimize the feed consumption required to produce eggs. Here, in trial A, pounds of feed per dozen eggs decreased by an average of 9.65% across the two trial flocks compared to the control flock. In trial B, pounds of feed per dozen eggs produced decreased by 3.04%, and in trial C, pounds of feed per dozen eggs decreased by 2.65%.

With respect to mortality, it is again noted that, throughout the egg laying production cycle, hens die due to a variety of reasons. Mortality is a meaningful metric in the egg production industry due to the opportunity cost of the lost production due to deceased hens. It is desirable to minimize mortality. Here, in trial A, mortality decreased an average of 8.33% comparing the average of the two test flocks to the control flock. In trial B, mortality decreased 2.21% comparing test flock to control flock, and in trial C, data was inconclusive.

As used herein, "seawater fluid" and "seawater concentrate" are interchangeable and defined as a fluid having a chemical composition substantially similar to ocean water. To this end, it is noted that such seawater fluid can be ascertained "naturally" (i.e., directly from the world's oceans), "artificially" (i.e., by producing a fluid with chemical properties substantially similar to ocean water), and/or any combination therein. It is further noted that ocean water includes a combination of all/most of the elements in the periodic table. Accordingly, in a first embodiment, the disclosed seawater fluid includes all elements in the periodic table. In another embodiment, however, the disclosed seawater fluid includes a majority of the elements in the periodic table. Furthermore, although the exact ratios may vary, Table T-1 below illustrates an exemplary concentration of elements in a seawater fluid.

TABLE T-1

| Symbol | Element Name | Seawater Concentration Parts per Million (PPM) |
|---|---|---|
| H+ | Hydrogen | Ultra-trace |
| Cl− | Chloride | 19,400.000000000 |
| Na | Sodium | 10,800.000000000 |
| Mg | Magnesium | 1,280.000000000 |
| $SO_4-$ | Sulfate | 898.000000000 |
| Ca | Calcium | 412.000000000 |
| K | Potassium | 399.000000000 |
| Br | Bromine | 67.000000000 |
| C | Carbon | 27.000000000 |
| $N_2$ | Nitrogen | 8.300000000 |
| Sr | Strontium | 7.800000000 |
| B | Boron | 4.500000000 |
| $O_2$ | Oxygen | 2.800000000 |
| Si | Silicon | 2.800000000 |
| F | Fluorine | 1.300000000 |
| Ar | Argon | 0.620000000 |
| $NO_3$ | Nitrate | 0.420000000 |
| Li | Lithium | 0.180000000 |
| Rb | Rubidenum | 0.120000000 |
| $PO_4$ | Phosphate | 0.620000000 |
| I | Iodine | 0.058000000 |
| Ba | Barium | 0.015000000 |
| Mo | Molybdenum | 0.010000000 |
| U | Uranium | 0.003200000 |
| V | Vanadium | 0.002000000 |
| As | Arsenic | 0.001200000 |
| Ni | Nickel | 0.000480000 |
| Zn | Zinc | 0.000350000 |
| Kr | Krypton | 0.000310000 |
| Cs | Cesium | 0.000306000 |
| Cr(VI) | Chromium | 0.000210000 |
| Sb | Antimony | 0.000200000 |
| Ne | Neon | 0.000160000 |
| Se | Selenium | 0.000155000 |
| Cu | Copper | 0.000150000 |
| Cd | Cadmium | 0.000070000 |
| Xe | Xenon | 0.000066000 |
| Al | Aluminum | 0.000030000 |
| Fe | Iron | 0.000030000 |
| Mn | Manganese | 0.000020000 |
| Y | Yttrium | 0.000017000 |
| Zr | Xircon | 0.000015000 |
| Tl | Thallium | 0.000013000 |
| W | Tungsten | 0.000010000 |
| Re | Rhenium | 0.000007800 |
| He | Helium | 0.000007600 |
| Ti | Titanium | 0.000006500 |
| La | Lanthanum | 0.000005600 |
| Ge | Germanium | 0.000005500 |
| Nb | Nobelium | 0.000005000 |
| Hf | Hafnium | 0.000003400 |
| Nd | Neodymium | 0.000003300 |
| Pb | Lead | 0.000002700 |
| Ta | Tantalum | 0.000002500 |
| Ag | Silver | 0.000002000 |
| Co | Cobalt | 0.000001200 |
| Ga | Gallium | 0.000001200 |
| Er | Erbium | 0.000001200 |
| Yb | Ytterbium | 0.000001200 |
| Dy | Dysprosium | 0.000001100 |
| Gd | Gadolinium | 0.000000900 |
| Sc | Scabdium | 0.000000700 |
| Ce | Cesium | 0.000000700 |
| Pr | Promethium | 0.000000700 |
| Sm | Samarium | 0.000000570 |

TABLE T-1-continued

| Symbol | Element Name | Seawater Concentration Parts per Million (PPM) |
|---|---|---|
| Sn | Tin | 0.000000500 |
| Ho | Holmium | 0.000000360 |
| Lu | Lutetium | 0.000000230 |
| Be | Beryllium | 0.000000210 |
| Tm | Thulium | 0.000000200 |
| Eu | Europium | 0.000000170 |
| Tb | Terbium | 0.000000170 |
| Hg | Mercury | 0.000000140 |
| Rh | Rhodium | 0.000000080 |
| Te | Tellurium | 0.000000070 |
| Pd | Palladium | 0.000000060 |
| Pt | Platinum | 0.000000050 |
| Bi | Bismuth | 0.000000030 |
| Th | Thorium | 0.000000020 |
| In | Indium | 0.000000010 |
| Au | Gold | 0.000000010 |
| Ru | Ruthium | 0.000000005 |
| Os | Osmium | 0.000000002 |
| Ir | Iridium | Ultra-trace |
| Ra | Radium | Ultra-trace |
| Rn | Radon | Ultra-trace |
| Fr | Francium | Ultra-tract |
| Ac | Actinium | Ultra-tract |
| Pa | Protactinium | Ultra-trace |

Referring next to FIG. 1, a block diagram of exemplary processes for utilizing a seawater fluid according to an embodiment is provided. As illustrated, system 100 includes a plurality of mineralization processes which facilitate optimizing various egg-production characteristics. For instance, a chicken feed process 122 is contemplated for converting conventional chicken feed 112 into mineralized chicken feed 132, a drinking water process 124 is contemplated for converting conventional chicken drinking water 114 into mineralized chicken drinking water 134, and a produce process 126 is contemplated for converting conventional produce 116 into mineralized produce 136. Each of these processes is discussed in more detail below.

Figure 2:
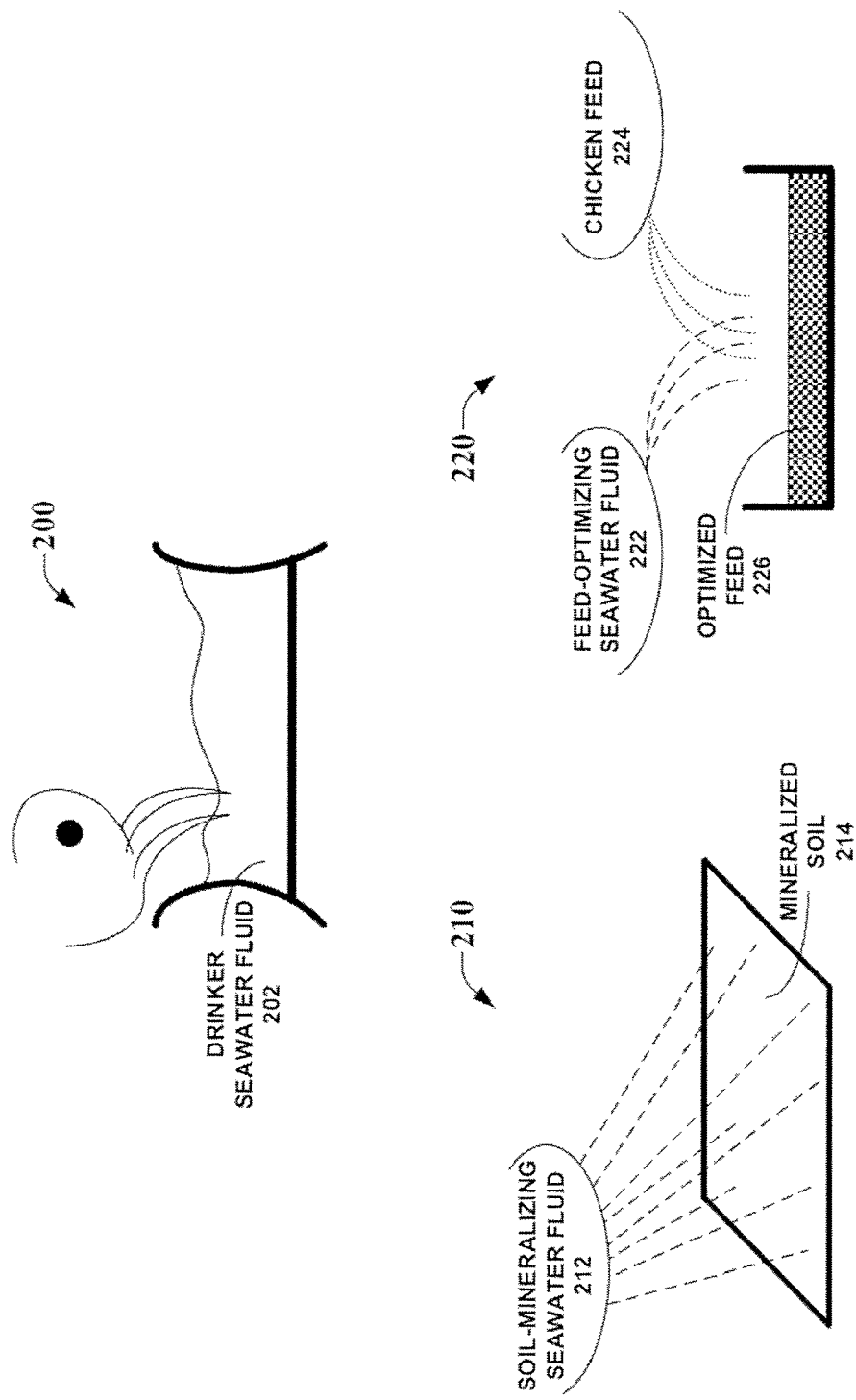
FIG. 2 illustrates various exemplary implementations for a seawater fluid according to an embodiment.

Referring next to FIG. 2, exemplary implementations for a seawater fluid according to an embodiment are provided. As illustrated, a first seawater fluid implementation 200 is directed towards a drinker seawater fluid 202. Within such embodiment, rather than utilizing conventional chicken drinking water, chickens are provided with drinker seawater fluid 202 to facilitate optimizing various egg-production characteristics. To this end, it should be appreciated that drinker seawater fluid 202 is generally analogous to mineralized chicken drinking water 134, wherein drinker seawater fluid 202 can be provided to chickens according to any of a plurality of protocols/ratios. For instance, in an exemplary embodiment, 3.5-42 ounces of a seawater concentrate (derived via any of the aspects disclosed herein) are mixed into 550 gallons of conventional chicken drinking water. Such a mixture can be used, for example, as a daily water source for approximately 10,000 chickens that is continuously available.

As further illustrated in FIG. 2, a second seawater fluid implementation 210 is directed towards a soil-mineralizing seawater fluid 212. Within such embodiment, rather than growing produce with conventional water, produce is grown on mineralized soil 214 which is conventional soil mineralized by soil-mineralizing seawater fluid 212. By growing produce on mineralized soil 214, mineralized produce generally analogous to mineralized produce 136 can be harvested and incorporated into chicken feed to facilitate optimizing various egg-production characteristics. For instance, in an exemplary embodiment, alfalfa may be grown on mineralized soil 214, wherein an acre of mineralized soil 214 can be ascertained by mineralizing an acre of conventional soil with 0.1-0.5 gallons of soil-mineralizing seawater fluid 212 (e.g., 0.1-0.5 gallons of seawater).

In another aspect illustrated in FIG. 2, a third seawater fluid implementation 220 is directed towards a feed-optimizing seawater fluid 222. For this particular embodiment, it is contemplated that feed-optimizing seawater fluid 222 may be applied to chicken feed 224 so as to produce optimized feed 226. Optimized feed 226 can then be incorporated into a flock's feeding protocol to facilitate optimizing various egg-production characteristics.

In an aspect, it should be noted that generating either of drinker seawater fluid 202, soil-mineralizing seawater fluid 212, feed-optimizing seawater fluid 222, and/or any other seawater fluid may involve determining a customized ratio of seawater to non-seawater fluid corresponding to a desired egg production optimization. Such embodiment may further comprise adjusting the customized ratio according to a different egg production optimization, and/or varying the customized ratio according to a usage type (e.g., a drinking water usage, a chicken feed usage, a soil mineralization usage, etc.). It is also contemplated that multiple desired egg production optimizations can be identified, wherein the customized ratio corresponds to the multiple desired egg production optimizations.

Figure 3:
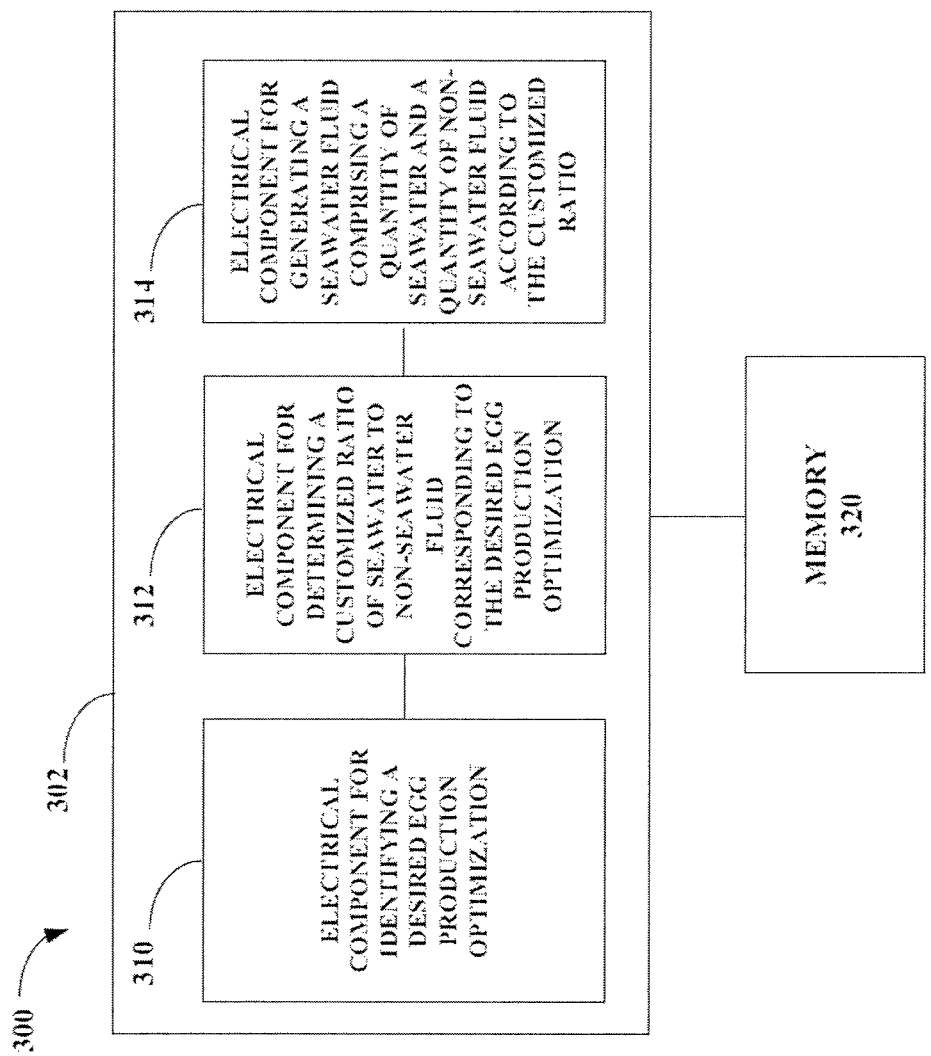
FIG. 3 illustrates an exemplary coupling of electrical components that effectuate generating a seawater fluid according to an embodiment.

Turning to FIG. 3, illustrated is a system 300 that facilitates generating a seawater fluid according to an embodiment. System 300 and/or instructions for implementing system 300 can reside within a computing device, for example. As depicted, system 300 includes functional blocks that can represent functions implemented by a processor using instructions and/or data from a computer readable storage medium. System 300 includes a logical grouping 302 of electrical components that can act in conjunction. As illustrated, logical grouping 302 can include an electrical component for identifying a desired egg production optimization 310. Furthermore, logical grouping 302 can include an electrical component for determining a customized ratio of seawater to non-seawater fluid corresponding to the desired egg production optimization 312. Logical grouping 302 can also include an electrical component for generating a seawater fluid comprising a quantity of seawater and a quantity of non-seawater fluid according to the customized ratio 314. Additionally, system 300 can include a memory 320 that retains instructions for executing functions associated with electrical components 310, 312, and 314. While shown as being external to memory 320, it is to be understood that electrical components 310, 312, and 314 can exist within memory 320.

Figure 4:
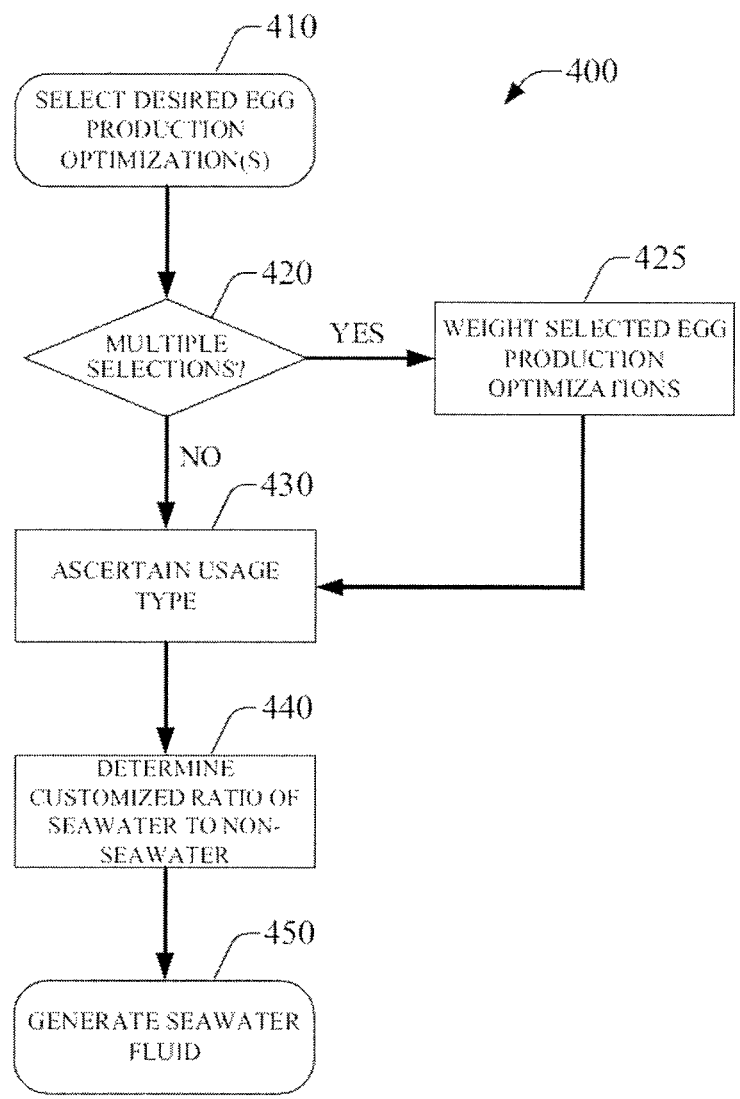
FIG. 4 illustrates a flow diagram of an exemplary methodology for generating a seawater fluid in accordance with an aspect of the subject specification.

Referring next to FIG. 4, a flow chart illustrating an exemplary method to facilitate generating a seawater fluid is provided. As illustrated, process 400 includes a series of acts that may be performed within a computing device according to an aspect of the subject specification. For instance, process 400 may be implemented by employing a processor to execute computer executable instructions stored on a computer readable storage medium to implement the series of acts. In another embodiment, a computer-readable storage medium comprising code for causing at least one computer to implement the acts of process 400 are contemplated.

In an aspect, process 400 begins with desired egg-production optimizations being selected at act 410. Here, it should be appreciated that single and/or multiple optimizations may be selected. For this particular embodiment, process 400 thus continues to act 420 where a determination is made as to whether multiple optimizations have been selected. If multiple optimizations are indeed selected, process 400 proceeds to act 425 where the selected egg-production optimizations are weighted relative to each other. To this end, it should be noted that weights can be determined in any of a plurality of ways. For instance, it is contemplated that user-based prioritization weights may be assigned to the selected optimizations, as well as default weights. User-based prioritization weights, for example, may be derived from a user's ranking of the selected optimizations and/or from a user's actual weighting of such optimizations. Alternatively, if no relative preferences are provided by a user, a default weighting system can be implemented where the selected optimizations are generally weighted evenly.

Once the prioritization weights are determined, or if multiple optimizations are not selected, process 400 proceeds to act 430 where a type of usage for the seawater fluid is ascertained. As stated previously, the seawater fluid described herein can facilitate egg-production optimizations via any of a plurality of implementations including, for example, having hens drink the seawater fluid (voluntarily and/or involuntarily), growing chicken feed crops on soil mineralized with the seawater fluid, and/or applying the seawater fluid onto conventional chicken feed.

After determining the application type, process 400 continues to act 440 where a customized ratio of seawater to non-seawater is determined. Here, it should be noted that such ratio can vary depending on any of a plurality of factors including, for example, the selected egg-production optimization(s), type of application, etc. To facilitate determining ratios, it is contemplated that a lookup table may be utilized. Once the customized ratio has been determined, process 400 then concludes with a seawater fluid generated according to the customized ratio at act 450.

Figure 5:
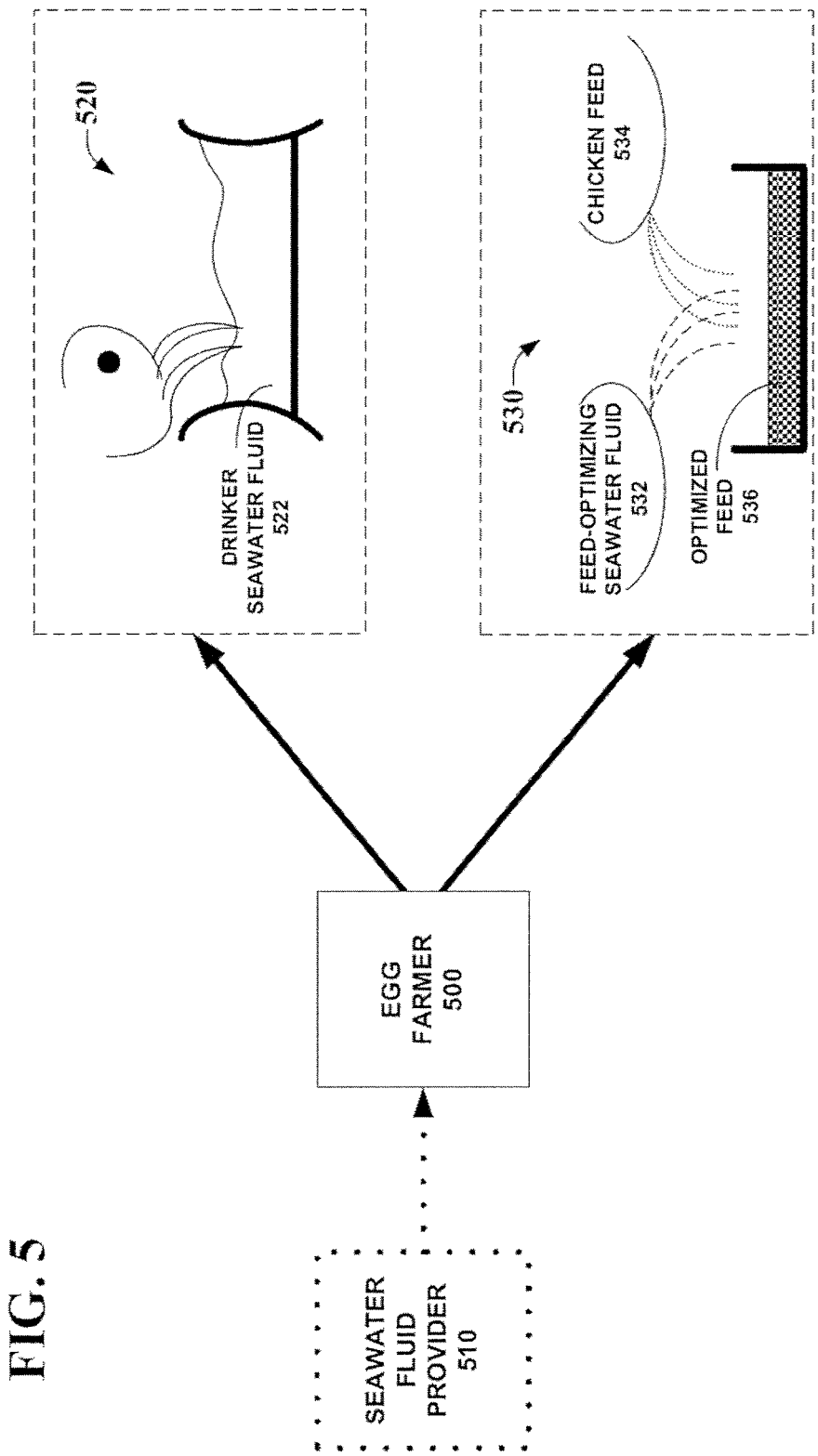
FIG. 5 illustrates exemplary egg-farming utilizations of a seawater fluid according to an embodiment.

Referring next to FIG. 5, exemplary egg-farming utilizations of a seawater fluid according to an embodiment are provided. Here, it should be appreciated that seawater fluids can be mixed by egg farmer 500 and/or provided to egg farmer 500 by seawater fluid provider 510. As illustrated, a first egg-farming utilization 520 is directed towards a drinker seawater fluid 522. Within such embodiment, chickens are provided with drinker seawater fluid 522 to facilitate optimizing various egg-production characteristics. To this end, it should be appreciated that drinker seawater fluid 522 is generally analogous to mineralized chicken drinking water 134 and drinker seawater fluid 202, wherein drinker seawater fluid 522 can be provided to chickens according to any of a plurality of protocols/ratios. It should be further appreciated that an automated system for incorporating drinker seawater fluid 522 can be implemented including, for example, having drinker seawater fluid 522 continuously injected via a water pump.

In another aspect illustrated in FIG. 5, a second egg-farming utilization 530 is directed towards a feed-optimizing seawater fluid 532. For this particular embodiment, it is contemplated that feed-optimizing seawater fluid 532 may be applied to chicken feed 534 so as to produce optimized feed 536. Optimized feed 536 can then be incorporated into a flock's feeding protocol to facilitate optimizing various egg-production characteristics.

It should be noted that utilizing either of drinker seawater fluid 522, feed-optimizing seawater fluid 532, and/or any other seawater fluid may thus involve providing such seawater fluid to at least one hen in any of a plurality of ways. For instance, the providing may comprise providing the seawater fluid as an exclusive drinking water source available to the at least one hen, and customizing a drinking protocol according to at least one desired egg production optimization. In another aspect, the providing may comprise applying a seawater fluid onto a feed provided to at least one hen.

Figure 6:
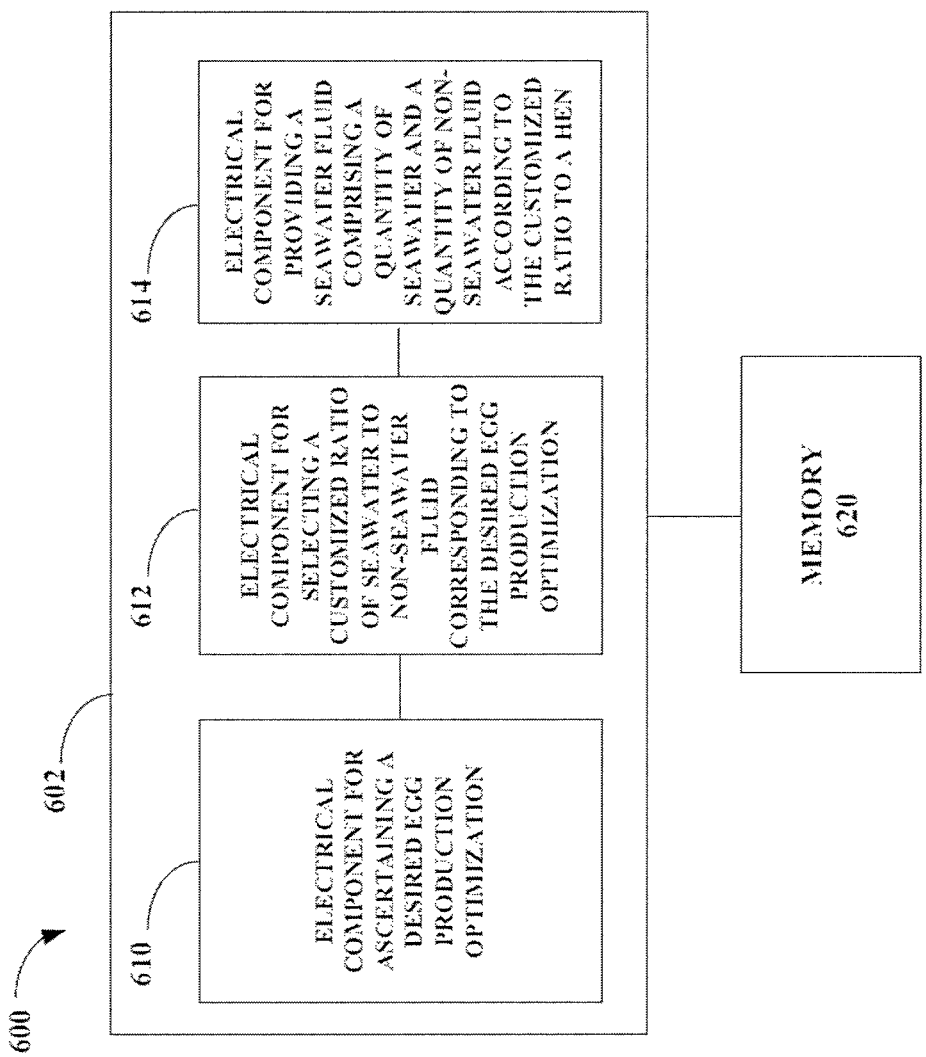
FIG. 6 illustrates an exemplary coupling of electrical components that effectuate utilizing a seawater fluid according to an embodiment.

Referring next to FIG. 6, illustrated is an exemplary system 600 that facilitates utilizing a seawater fluid according to an embodiment. System 600 and/or instructions for implementing system 600 can physically reside within a computing device, for instance, wherein system 600 includes functional blocks that can represent functions implemented by a processor using instructions and/or data from a computer readable storage medium. System 600 includes a logical grouping 602 of electrical components that can act in conjunction similar to logical grouping 302 in system 300. As illustrated, logical grouping 602 can include an electrical component for ascertaining a desired egg production optimization 610. Furthermore, logical grouping 602 can include an electrical component for selecting a customized ratio of seawater to non-seawater fluid corresponding to the desired egg production optimization 612. Logical grouping 602 can also include an electrical component for providing a seawater fluid comprising a quantity of seawater and a quantity of non-seawater fluid according to the customized ratio to a hen 614. Additionally, system 600 can include a memory 620 that retains instructions for executing functions associated with electrical components 610, 612, and 614. While shown as being external to memory 620, it is to be understood that electrical components 610, 612, and 614 can exist within memory 620.

Figure 7:
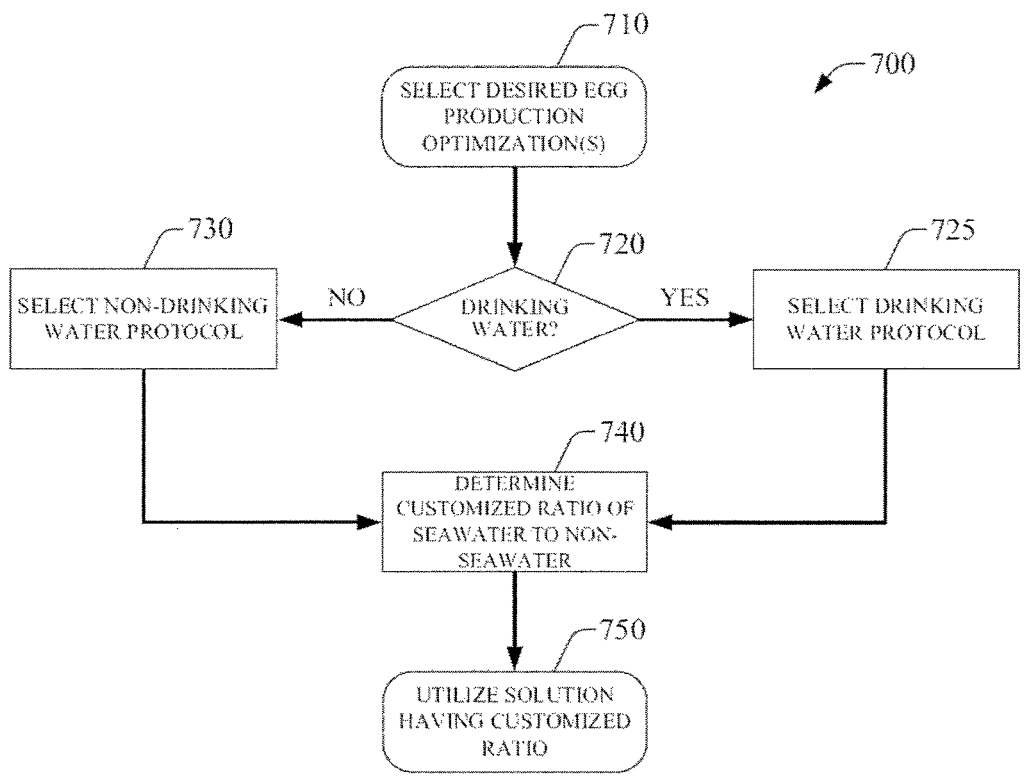
FIG. 7 illustrates a flow diagram of an exemplary methodology for utilizing a seawater fluid in accordance with an aspect of the subject specification.

Referring next to FIG. 7, a flow chart illustrating an exemplary method to facilitate utilizing a seawater fluid is provided. As illustrated, process 700 includes a series of acts that may be performed within a computing device according to an aspect of the subject specification. For instance, process 700 may be implemented by employing a processor to execute computer executable instructions stored on a computer readable storage medium to implement the series of acts. In another embodiment, a computer-readable storage medium comprising code for causing at least one computer to implement the acts of process 700 are contemplated.

In an aspect, process 700 begins with desired egg-production optimizations being selected at act 710. Here, as stated previously, it is contemplated that the disclosed seawater fluid can be utilized within a drinking water context and/or a non-drinking water context. For this particular embodiment, process 700 thus continues to act 720 where a determination is made as to whether a drinking water implementation is desired. If a drinking water implementation is indeed desired, process 700 proceeds to act 725 where a particular drinking water protocol is selected. Here, drinking water protocols may include a voluntary/involuntary drinking designation, an optimization-specific drinking frequency/quantity, etc. However, if act 720 determines that a non-drinking water implementation is desired, process 700 proceeds to act 730 where a particular non-drinking water protocol is selected. Here, such non-drinking water protocols may include designating a usage type (e.g., utilizing a seawater fluid to mineralize soil, spray onto a conventional feed, etc.) and/or identifying an optimization-specific application frequency/quantity.

After determining the appropriate protocol, process 700 continues to act 740 where a customized ratio of seawater to non-seawater is determined. Here, it should be noted that such ratio can vary depending on any of a plurality of factors including, for example, the selected egg-production optimization(s), type of use, etc. As stated previously, to facilitate determining ratios, it is contemplated that a lookup table may be utilized. Once the customized ratio has been determined, process 700 then concludes at act 750 with a utilization of a seawater fluid having the customized ratio determined at act 740.

Figure 8:
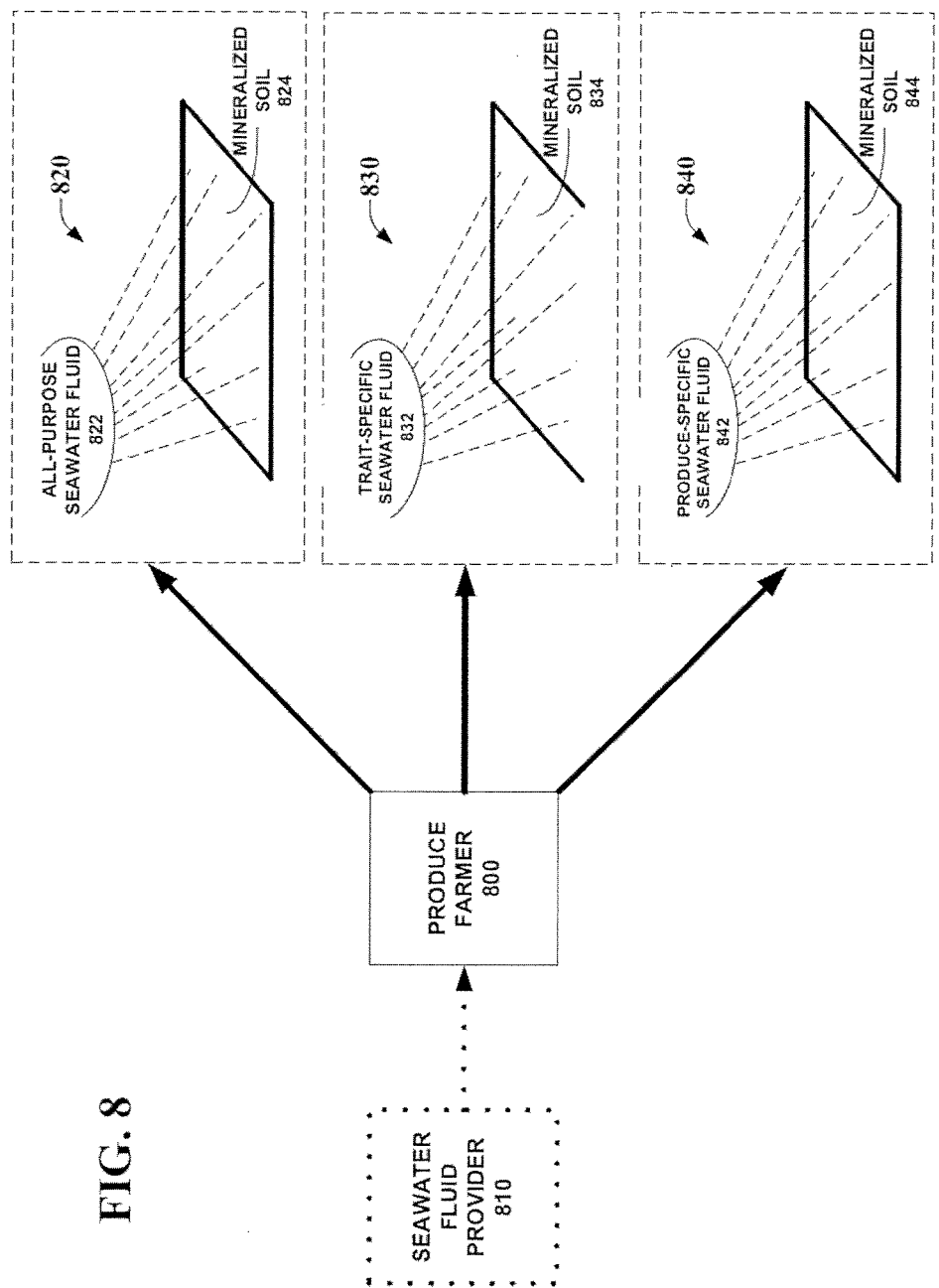
FIG. 8 illustrates exemplary produce-mineralizing utilizations of a seawater fluid according to an embodiment.

Referring next to FIG. 8, exemplary produce-mineralizing utilizations of a seawater fluid according to an embodiment are provided. Here, it should be appreciated that seawater fluids can be mixed by produce farmer 800 and/or provided to produce farmer 800 by seawater fluid provider 810. As illustrated, a first produce-mineralizing utilization 820 is directed towards mineralizing soil with an all-purpose seawater fluid 822 to yield mineralized soil 824. Within such embodiment, a default ratio of seawater to non-seawater fluid can be used to facilitate a generic egg production optimization. However, it is also contemplated that customized seawater fluids can be ascertained by modifying the default ratio. For instance, a second produce-mineralizing utilization 830 is directed towards mineralizing soil with a trait-specific seawater fluid 832 to yield mineralized soil 834, wherein trait-specific seawater fluid 832 can be ascertained by modifying a default ratio of seawater to non-seawater fluid according to at least one preferred egg production optimization. A third produce-mineralizing utilization 840 is also contemplated and directed towards mineralizing soil with a produce-specific seawater fluid 842 to yield mineralized soil 844, wherein the ratio of seawater to non-seawater fluid is variable according to a produce type (e.g., an alfalfa-specific ratio).

In an aspect, it is noted that a customized ratio of seawater to non-seawater fluid can be determined in various ways. For instance, such determination may comprise selecting the customized ratio from a lookup table, wherein any of various egg production optimizations may be listed, and wherein each optimization (or set of optimizations) has a corresponding ratio of seawater to non-seawater fluid. Furthermore, since it may also be desirable to utilize non-seawater nutrients, it is contemplated that determining a particular ratio may further comprise ascertaining a nutrient ratio corresponding to at least one preferred egg production optimization, and incorporating nutrients into a quantity of non-seawater fluid according to the nutrient ratio.

It is further noted that any of various application protocols can be implemented to facilitate mineralizing soil according to the aspects described herein. For instance, it is contemplated that such mineralizing may comprise applying a seawater fluid onto a plot of soil according to a particular application protocol, wherein the application protocol corresponds to at least one preferred egg production optimization. Moreover, it is contemplated that an application protocol which identifies any of various characteristics for applying a seawater fluid (e.g., application frequency, application density, etc.), can be customized to accentuate particular egg production optimizations.

An exemplary application protocol for facilitating an egg production optimization is now described. Here, it should be noted that such protocol may be modified according to the particular type of seawater fluid used (e.g., all-purpose seawater fluid 822, trait-specific seawater fluid 832, produce-specific seawater fluid 842, etc.). It should be further noted that such protocol can also be modified according to a desired optimization strength (e.g., applying more/less of a trait-specific seawater fluid directed towards egg shell hardness according to a particularly desired egg shell hardness).

In an aspect, a particular application protocol can include a first protocol for initially preparing soil, and a second protocol in preparation for growing each subsequent stand. An exemplary first and second protocol is now described for growing mineralized alfalfa according to an embodiment. To this end, although such protocols are described within the context of growing mineralized alfalfa, similar and/or modified protocols are contemplated for non-alfalfa produce as well.

Initially preparing the soil according to the first protocol may begin with the application of an effective microorganism (EM) solution via foliar spray, wherein 3-10 gallons of EM solution per acre may be used. Herbicide can also be applied, as needed. After approximately one week, another 3-10 gallons of EM solution per acre, in addition to 0.1-0.5 gallons of NitroCarb® per acre, may be applied. After approximately three days, the following may be nursed into the irrigation water: 1-5 gallons of Calganix® per acre; 0.1-0.5 gallons of seawater fluid per acre; 0.1-0.5 gallons of NitroCarb® per acre; and 1-5 gallons of fish fertilizer.

With respect to the second protocol directed towards growing subsequent crops of mineralized produce, an exemplary protocol is now described. After each cutting, the following may be incorporated into a plot's irrigation water: 1-5 gallons of EM solution per acre; 1-5 gallons of Calganix® per acre; 0.1-0.5 gallons of seawater fluid per acre; 0.1-0.5 gallons of NitroCarb® per acre; and 1-5 gallons of fish fertilizer.

Figure 9:
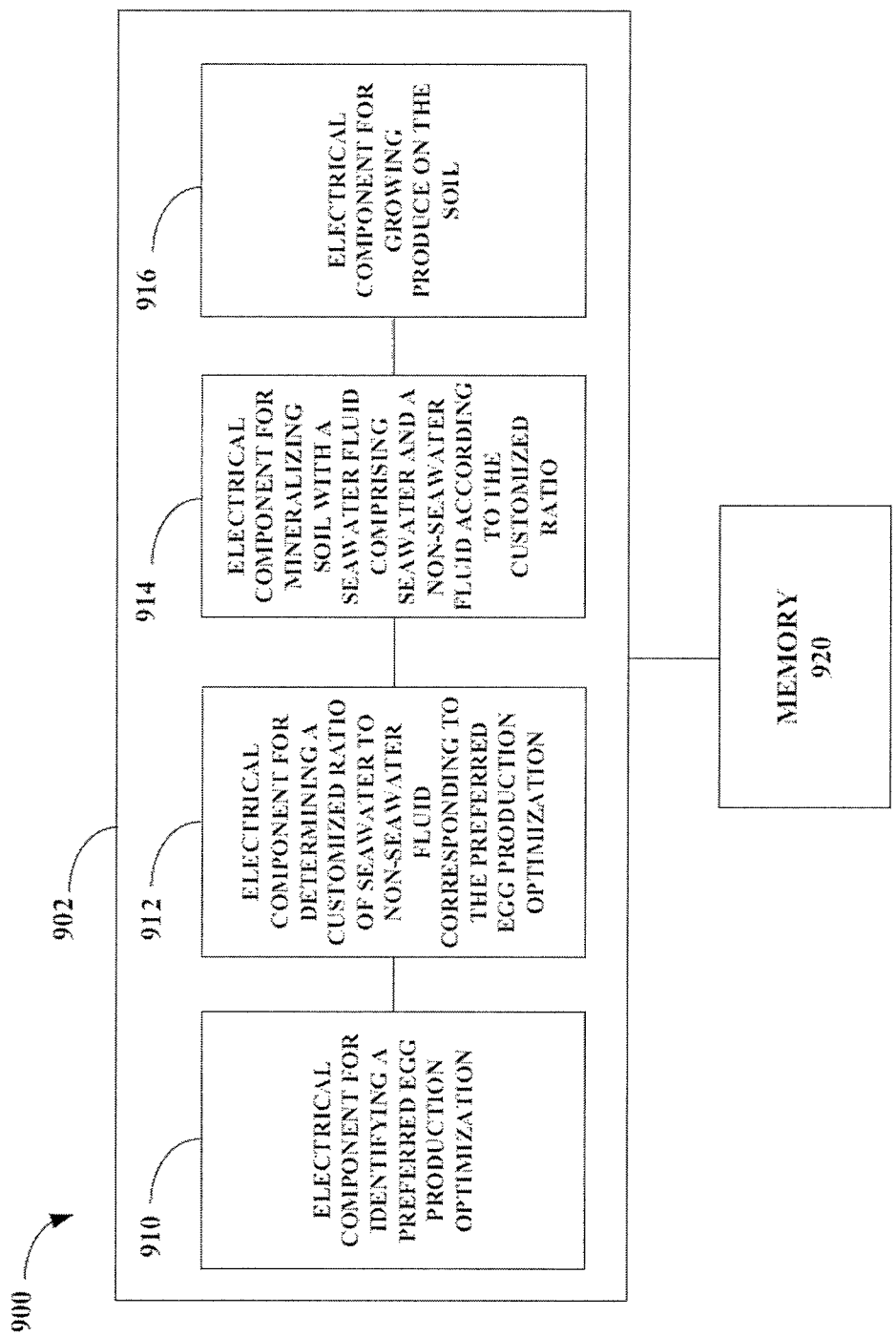
FIG. 9 illustrates an exemplary coupling of electrical components that effectuate mineralizing produce with a seawater fluid according to an embodiment.

Referring next to FIG. 9, illustrated is an exemplary system 900 that facilitates mineralizing produce with a seawater fluid according to an embodiment. System 900 and/or instructions for implementing system 900 can physically reside within a computing device, for instance, wherein system 900 includes functional blocks that can represent functions implemented by a processor using instructions and/or data from a computer readable storage medium. System 900 includes a logical grouping 902 of electrical components that can act in conjunction similar to logical groupings 302 and 602 respectively corresponding to systems 300 and 600. As illustrated, logical grouping 902 can include an electrical component for identifying a preferred egg production optimization 910, as well as an electrical component for determining a customized ratio of seawater to non-seawater fluid corresponding to the preferred egg production optimization 912. Logical grouping 902 can also include an electrical component for mineralizing soil with a seawater fluid comprising seawater and a non-seawater fluid according to the customized ratio 914. Further, logical grouping 902 can include an electrical component for growing produce on the soil 916. Additionally, system 900 can include a memory 920 that retains instructions for executing functions associated with electrical components 910, 912, 914, and 916. While shown as being external to memory 920, it is to be understood that electrical components 910, 912, 914, and 916 can exist within memory 920.

Figure 10:
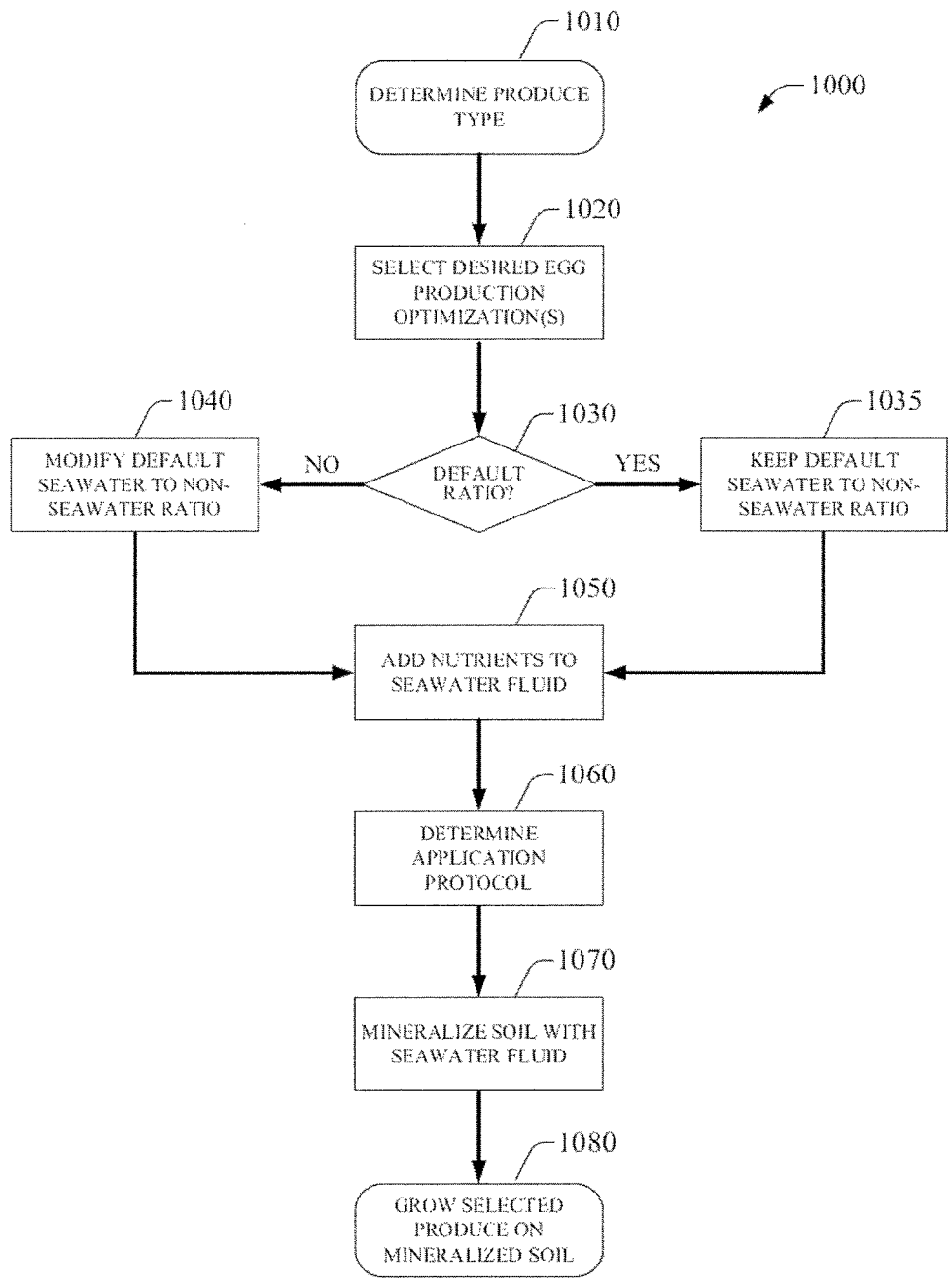
FIG. 10 illustrates a flow diagram of an exemplary methodology for mineralizing produce with a seawater fluid in accordance with an aspect of the subject specification.

Referring next to FIG. 10, a flow chart illustrating an exemplary method to facilitate mineralizing produce with a seawater fluid is provided. As illustrated, process 1000 includes a series of acts that may be performed within a computing device according to an aspect of the subject specification. For instance, process 1000 may be implemented by employing a processor to execute computer executable instructions stored on a computer readable storage medium to implement the series of acts. In another embodiment, a computer-readable storage medium comprising code for causing at least one computer to implement the acts of process 1000 are contemplated.

In an aspect, process 1000 begins with a type of produce (e.g., alfalfa) being determined at act 1010, and desired egg-production optimization(s) being selected at act 1010.

For this embodiment, process 1000 then proceeds to act 1020 where it determines whether to utilize a default ratio of seawater to non-seawater based on the selected produce type and egg-production optimization(s). If a default ratio is deemed adequate, the default ratio is accepted at act 1035. Otherwise, if the default ratio is deemed inadequate, a modification to the default ratio is made at act 1040.

For some embodiments, it may be desirable to further optimize egg-production characteristics by adding nutrients to a seawater fluid. Accordingly, once an appropriate ratio of seawater to non-seawater is determined, process 1000 proceeds to act 1050 where such nutrients are added.

In an aspect, it is contemplated that soil can be mineralized with the seawater fluid disclosed herein via any of a plurality of application protocols. For instance, depending on the particular type of produce type and/or egg-production optimization(s), such application protocols may vary with respect to application frequency/density. Process 1000 thus proceeds with the selection of the appropriate application protocol at act 1060, followed by a mineralization of soil performed according to the selected application protocol at act 1070. Process 1000 then concludes at act 1080 where produce is grown on the mineralized soil.

Figure 11:
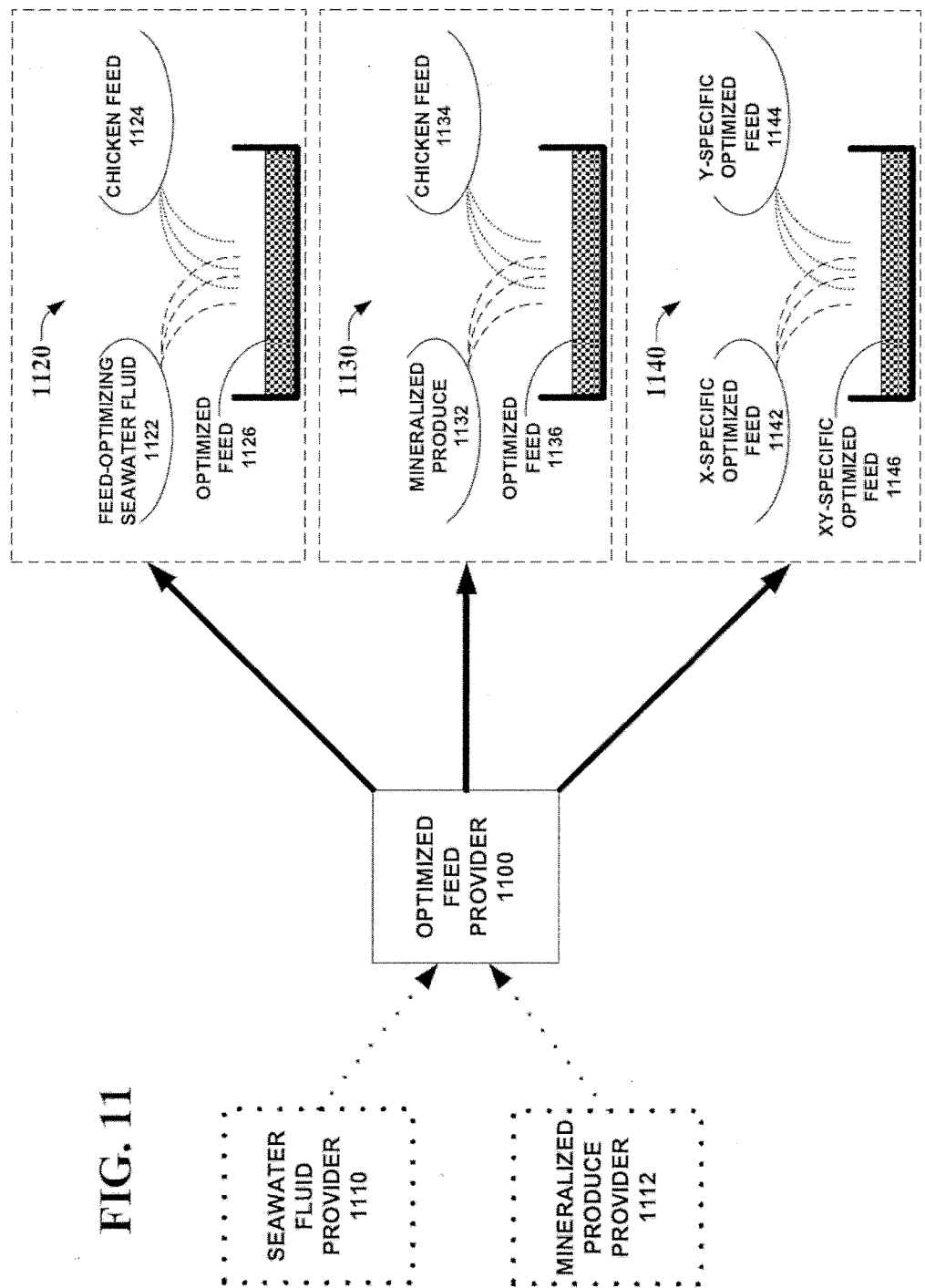
FIG. 11 illustrates exemplary feed-producing utilizations of a seawater fluid according to an embodiment.

Referring next to FIG. 11, exemplary feed-producing utilizations of a seawater fluid according to an embodiment are provided. Here, it should be appreciated that optimized feeds can be ascertained in various ways. As illustrated, a first feed-producing utilization 1120 is directed towards producing optimized feed 1126 by applying a feed-optimizing seawater fluid 1122 to conventional chicken feed 1124. For this particular embodiment, optimized feed provider 1100 may obtain feed-optimizing seawater fluid 1122 from seawater fluid provider 1110, as shown.

A second feed-producing utilization 1130 is also disclosed, which is directed towards producing optimized feed 1136 by mixing mineralized produce 1132 with conventional chicken feed 1134. Within such embodiment, optimized feed provider 1100 may obtain mineralized produce 1132 from mineralized produce provider 1112, as shown. Although any of a plurality of ratios of mineralized produce 1132 to conventional chicken feed 1134 can be used (e.g., to accentuate various egg production characteristics), it has been discovered that particularly desirable results are ascertained when optimized feed 1136 includes 1%-7.5% mineralized produce 1132 (e.g., mineralized alfalfa) and 92.5%-99% conventional chicken feed 1134.

Mixing different types of optimized feeds is also contemplated. For instance, as illustrated in FIG. 11, a third feed-producing utilization 1140 is also disclosed, which is directed towards producing a hybrid feed that optimizes multiple egg production characteristics by mixing different trait-specific optimized feeds. For this particular example, an X-specific optimized feed 1142 (e.g., a feed directed towards optimizing egg shell hardness) is mixed with a Y-specific optimized feed 1144 (e.g., a feed directed towards optimizing molting), so as to produce an XY-specific optimized feed 1146 (i.e., a hybrid feed directed towards optimizing egg shell hardness and molting).

In an aspect, it is noted that customized ratios for producing specific types of optimized feeds are contemplated. Such ratios may, for example, include a customized ratio of feed-optimizing seawater fluid 1122 to chicken feed 1124, a customized ratio of mineralized produce 1132 to chicken feed 1134, or a customized ratio of X-specific optimized feed 1142 to Y-specific optimized feed 1144. Determining particular ratios may comprise retrieving the customized ratio from a lookup table, wherein any of various egg production optimizations may be listed, and wherein customized ratios may be adjusted according to different egg production optimizations. Furthermore, since it may also be desirable to optimize multiple egg production characteristics, producing an optimized feed may include identifying multiple desired egg production optimizations, wherein the customized ratio corresponds to the multiple desired egg production optimizations. Such embodiment may then further include a mechanism to facilitate prioritizing egg production characteristics. For example, this embodiment may include determining a prioritization of the multiple desired egg production optimizations, and adjusting the customized ratio according to the prioritization. It is also contemplated that such embodiment may further comprise assigning a prioritization weight to at least one of the multiple desired egg production optimizations, wherein the adjusting comprises further adjusting the customized ratio according to the prioritization weight.

Figure 12:
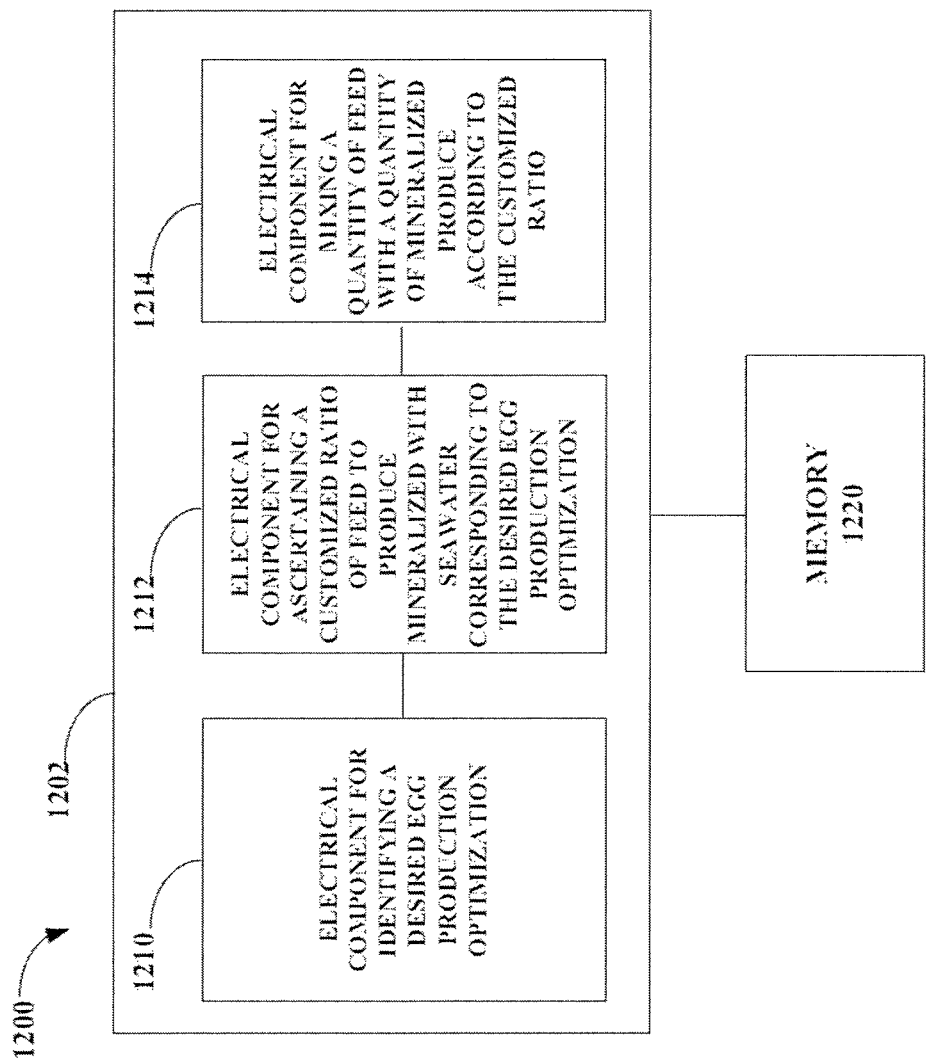
FIG. 12 illustrates an exemplary coupling of electrical components that effectuate producing an optimized chicken feed according to an embodiment.

Referring next to FIG. 12, illustrated is an exemplary system 1200 that facilitates producing an optimized chicken feed according to an embodiment. System 1200 and/or instructions for implementing system 1200 can physically reside within a computing device, for instance, wherein system 1200 includes functional blocks that can represent functions implemented by a processor using instructions and/or data from a computer readable storage medium. System 1200 includes a logical grouping 1202 of electrical components that can act in conjunction similar to logical groupings 302, 602, and 902 respectively corresponding to systems 300, 600, and 900. As illustrated, logical grouping 1202 can include an electrical component for identifying a desired egg production optimization 1210. Furthermore, logical grouping 1202 can include an electrical component for ascertaining a customized ratio of feed to produce mineralized with seawater corresponding to the desired egg production optimization 1212. Logical grouping 1202 can also include an electrical component for mixing a quantity of feed with a quantity of mineralized produce according to the customized ratio 1214. Additionally, system 1200 can include a memory 1220 that retains instructions for executing functions associated with electrical components 1210, 1212, and 1214. While shown as being external to memory 1220, it is to be understood that electrical components 1210, 1212, and 1214 can exist within memory 1220.

Figure 13:
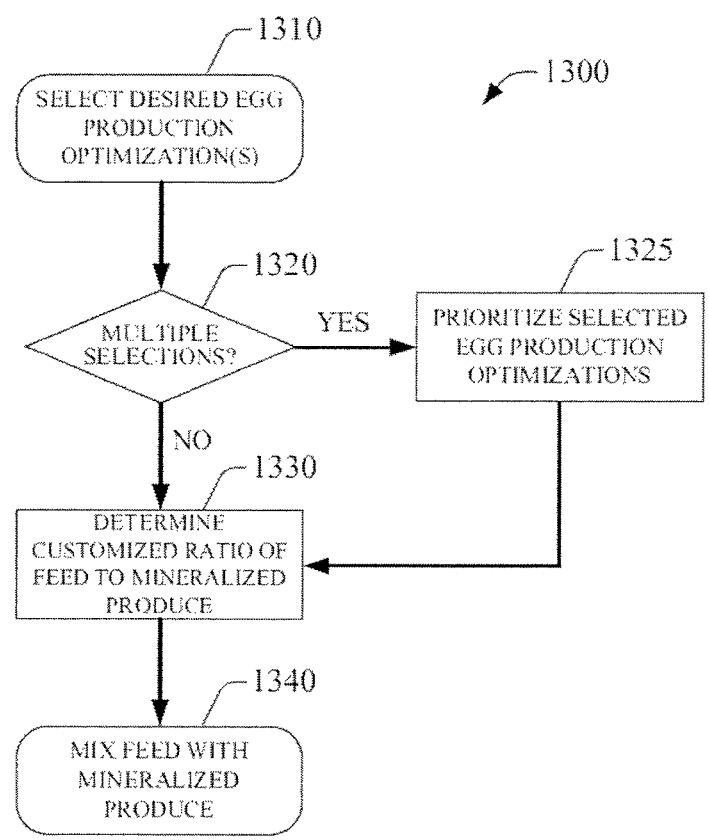
FIG. 13 illustrates a flow diagram of an exemplary methodology for producing an optimized chicken feed in accordance with an aspect of the subject specification.

Referring next to FIG. 13, a flow chart illustrating an exemplary method to facilitate producing an optimized chicken feed is provided. As illustrated, process 1300 includes a series of acts that may be performed within a computing device according to an aspect of the subject specification. For instance, process 1300 may be implemented by employing a processor to execute computer executable instructions stored on a computer readable storage medium to implement the series of acts. In another embodiment, a computer-readable storage medium comprising code for causing at least one computer to implement the acts of process 1300 are contemplated.

In an aspect, process 1300 begins with desired egg-production optimizations being selected at act 1310, wherein single and/or multiple optimizations may be selected. For this particular embodiment, process 1300 then continues to act 1320 where a determination is made as to whether multiple optimizations have been selected. If multiple optimizations are indeed selected, process 1300 proceeds to act 1325 where the selected egg-production optimizations are prioritized relative to each other. Here, any of a plurality of prioritization algorithms can be implemented. For instance, as stated previously, it is contemplated that user-based prioritization weights may be assigned to the selected optimizations, as well as default weights. User-based prioritization weights, for example, may be derived from a user's ranking of the selected optimizations and/or from a user's actual weighting of such optimizations. Alternatively, if no relative preferences are provided by a user, a default prioritization system can be implemented where the selected optimizations are generally prioritized evenly.

Once the prioritization weights are determined, or if multiple optimizations are not selected, process 1300 proceeds to act 1330 where a customized ratio of feed to mineralized produce is determined. Here, it should be noted that such ratio can vary depending on any of a plurality of factors including, for example, the selected egg-production optimization(s), various chicken/flock characteristics (e.g., age and/or breed), etc. To facilitate determining ratios, it is again contemplated that a lookup table may be utilized. Once the customized ratio has been determined, process 1300 then concludes at act 1350 with conventional feed being mixed with mineralized produce according to the customized ratio.

Figure 14:
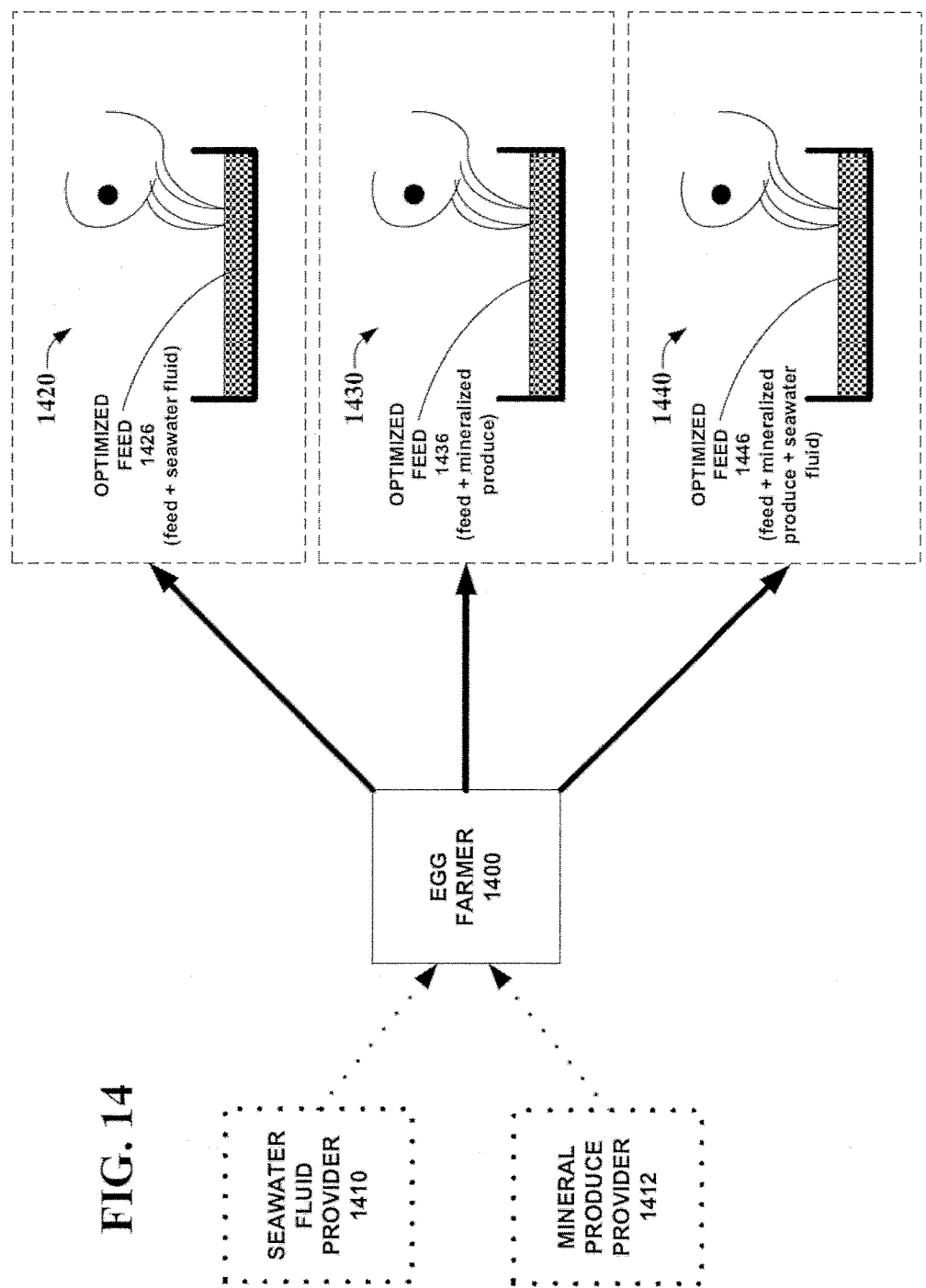
FIG. 14 illustrates exemplary utilizations of an optimized feed according to an embodiment.

Referring next to FIG. 14, exemplary utilizations of an optimized feed according to an embodiment are provided. Here, it should be appreciated that optimized feeds can be utilized in various ways. As illustrated, a first optimized feed utilization 1420 is directed towards providing chickens with optimized feed 1426, wherein optimized feed 1426 is a combination of conventional chicken feed and a seawater fluid. A second optimized feed utilization 1430 is directed towards providing chickens with optimized feed 1436, wherein optimized feed 1436 is a combination of conventional chicken feed and mineralized produce (e.g., alfalfa grown on soil mineralized with a seawater fluid). A third optimized feed utilization 1440 is also contemplated, which is directed towards providing chickens with optimized feed 1446, wherein optimized feed 1446 is a combination of conventional chicken feed, mineralized produce, and a seawater fluid.

In an aspect it contemplated that a desired egg production optimization is selected from a plurality of optimizations, wherein a ratio of chicken feed to mineralized produce and/or seawater fluid varies in each of the plurality of optimizations. Optimizations may, for example, be directed towards egg shell hardness, molting, and/or an egg consumption characteristic (e.g., a flavor characteristic, a cholesterol characteristic, a caloric characteristic, etc.). Furthermore, to facilitate ascertaining a particular optimization (or combination of optimizations), providing chickens with an optimized feed may comprise customizing a feeding protocol according to the desired egg production optimization(s).

Figure 15:
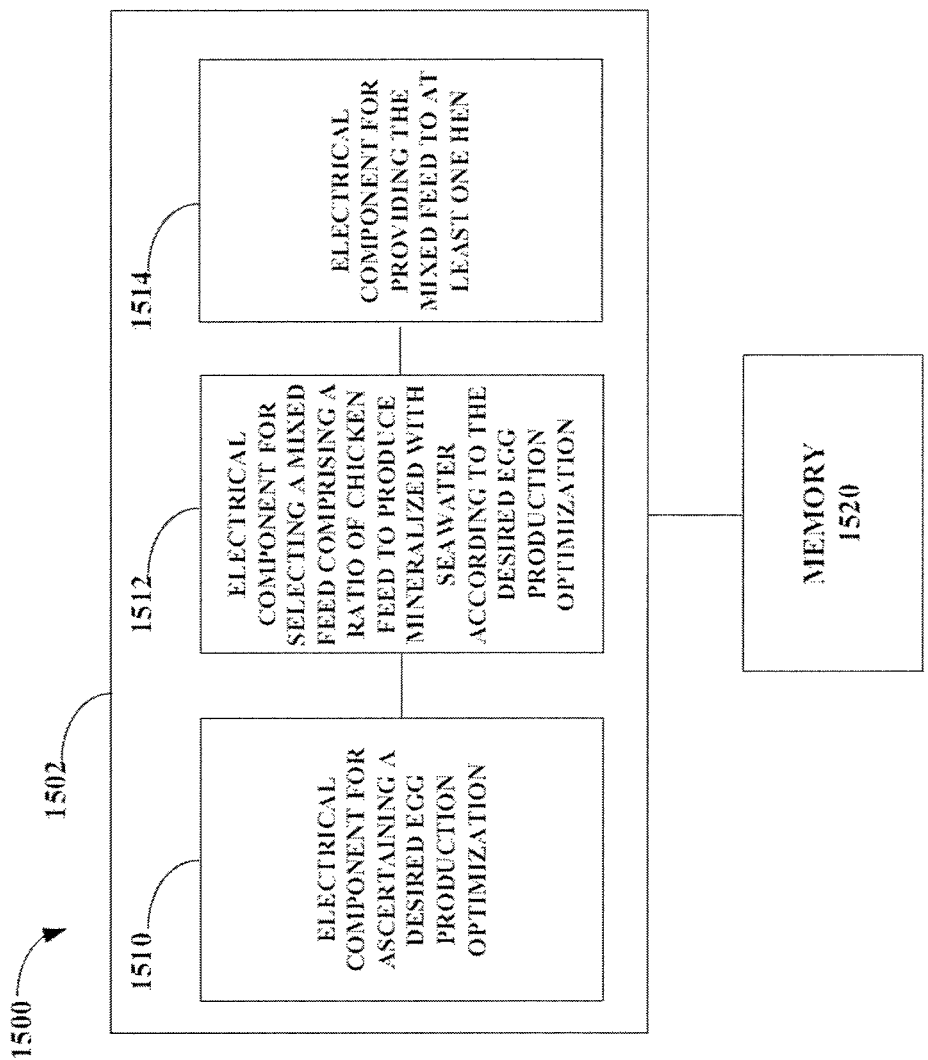
FIG. 15 illustrates an exemplary coupling of electrical components that effectuate utilizing an optimized chicken feed according to an embodiment.

Referring next to FIG. 15, illustrated is an exemplary system 1500 that facilitates utilizing an optimized chicken feed according to an embodiment. System 1500 and/or instructions for implementing system 1500 can physically reside within a computing device, for instance, wherein system 1500 includes functional blocks that can represent functions implemented by a processor using instructions and/or data from a computer readable storage medium. System 1500 includes a logical grouping 1502 of electrical components that can act in conjunction similar to logical groupings 302, 602, 902, and 1202 respectively corresponding to systems 300, 600, 900, and 1200. As illustrated, logical grouping 1502 can include an electrical component for ascertaining a desired egg production optimization 1510. Furthermore, logical grouping 1502 can include an electrical component for selecting a mixed feed comprising a ratio of chicken feed to produce mineralized with seawater according to the desired egg production optimization 1512. Logical grouping 1502 can also include an electrical component for providing the mixed feed to at least one hen 1514. Additionally, system 1500 can include a memory 1520 that retains instructions for executing functions associated with electrical components 1510, 1512, and 1514. While shown as being external to memory 1520, it is to be understood that electrical components 1510, 1512, and 1514 can exist within memory 1520.

Figure 16:
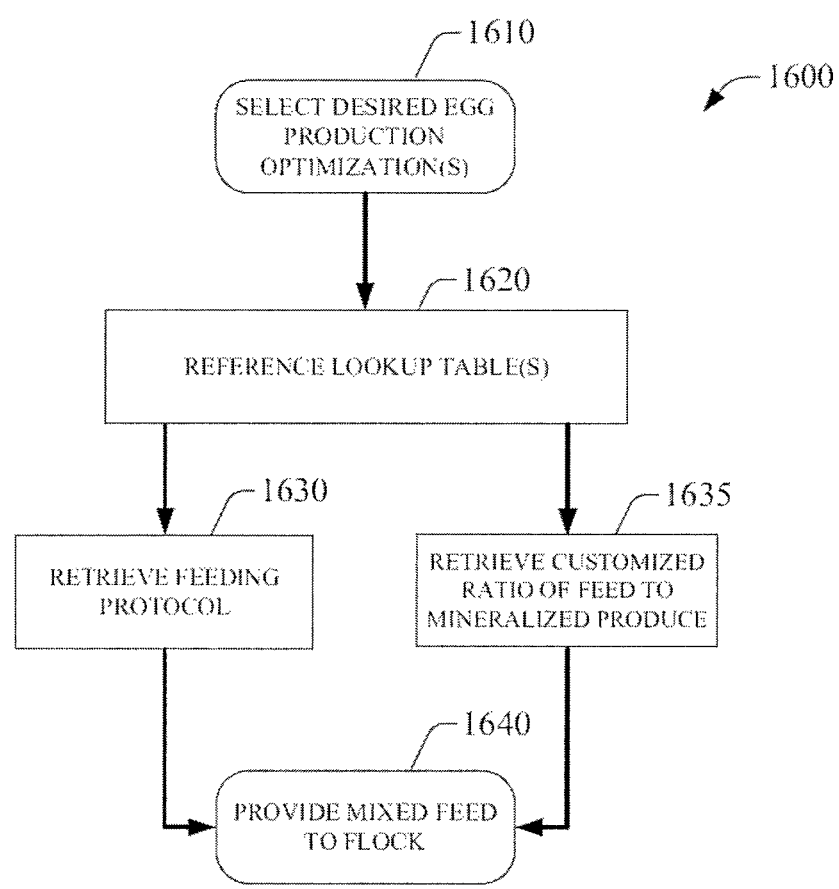
FIG. 16 illustrates a flow diagram of an exemplary methodology for utilizing an optimized chicken feed in accordance with an aspect of the subject specification.

Referring next to FIG. 16, a flow chart illustrating an exemplary method to facilitate utilizing an optimized chicken feed is provided. As illustrated, process 1600 includes a series of acts that may be performed within a computing device according to an aspect of the subject specification. For instance, process 1600 may be implemented by employing a processor to execute computer executable instructions stored on a computer readable storage medium to implement the series of acts. In another embodiment, a computer-readable storage medium comprising code for causing at least one computer to implement the acts of process 1600 are contemplated.

In an aspect, process 1600 begins with desired egg-production optimizations being selected at act 1610. Based on the selected egg-production optimizations, a lookup table can then be referenced at act 1620 to ascertain utilization details which facilitate yielding such optimizations. For instance, a first lookup table can be referenced to retrieve a feeding protocol (e.g., feeding frequency/quantity) corresponding to a particular optimization at act 1630, whereas a second lookup table can be referenced to retrieve a customized ratio of feed to mineralized produce corresponding to the same optimization at act 1635. A mixed feed comprising the customized ratio of feed to mineralized produce can then be provided to a chicken flock at act 1640 according to the appropriate feeding protocol.

In another aspect, it is contemplated that extracting/creating a seawater concentrate having particular characteristics will be desirable. To this end, it is noted that at least eighty-nine elements and minerals (See Table T-1) have been identified in sea/ocean water as being particularly relevant, either alone or in various combinations, to facilitate the egg-production optimizations described herein. Of these eighty-nine minerals and elements, seven are deemed "major" herein based on their abundance in mammals. In order of abundance, those minerals/elements are Calcium, Phosphorus, Potassium, Sulfur, Sodium, Chlorine, and Magnesium. In one aspect, it has been discovered that creating a seawater concentrate that includes at least these seven minerals/elements facilitates the various egg production optimizations disclosed herein. Furthermore, of the eighty-nine minerals and elements listed in Table T-1, thirteen have been identified herein as being particularly important to biological processes, wherein those minerals/elements include Potassium, Chlorine, Sodium, Calcium, Phosphorus, Magnesium, Zinc, Iron, Manganese, Copper, Iodine, Selenium, and Molybdenum. In another aspect, it has been discovered that creating a seawater concentrate that includes at least these thirteen minerals/elements also facilitates the various egg production optimizations disclosed herein.

It should be noted that determining the efficacy of a seawater dosage protocol may include ascertaining whether hens exhibit adequate levels of the aforementioned thirteen minerals/elements deemed important to biological processes. Such efficacy may also be determined via a cause and effect type analysis, i.e. if the hen displays a certain symptom associated with deficiency of a particular mineral/element, the content of the seawater fluid may be adjusted so that the specific mineral/element in question is raised/lowered in the hen to a desired level. For instance, a seawater dosage protocol may be used to increase calcium levels in egg laying hens to support the demands that increased egg production places on the laying birds.

In another aspect, a full spectrum dosage of the eighty-nine minerals and elements listed in Table T-1 is contemplated. Indeed, in order to more closely emulate naturally occurring seawater, each of the eighty-nine minerals/elements might be included in a synthetic seawater fluid as described herein. To this end, because naturally occurring seawater also includes particular bioactive enzymes, some embodiments may include producing a seawater fluid to include such enzymes as well.

It is further noted that, although producing a synthetic seawater fluid is contemplated in one embodiment, producing a seawater concentrate from a seawater sample is also contemplated in another embodiment. Indeed, because a hen's body may treat synthetic minerals/elements as xenobiotic compounds, a hen's body may reject these minerals/elements and excrete them. Moreover, because the hen's body may not recognize these minerals/elements, they might be treated as toxins. For some applications, producing a seawater concentrate from a seawater sample may thus be more desirable.

Details directed towards producing a seawater concentrate are now discussed. It has been observed that minerals and organic constituents exist in approximately the same proportion, wherein approximately 3.5% of seawater is comprised of these constituents, and wherein the same approximate ratio is found in all oceans and seas. The exception is phosphorus which has higher relative levels in the Pacific Ocean due to volcanic activity, wherein no beneficial/detrimental effect of this additional phosphorus is noted, however. Also, with respect to measuring mineral/element levels, it is noted that a single assay method will not suffice to detect every mineral/element listed in Table T-1. However, many of the minerals/elements can be detected and measured via Inductively Coupled Plasma Mass Spectrometry (ICP-MS).

The seawater concentrate/fluid disclosed herein can be derived via any of a plurality of processes. For instance, such processes may include, but are not limited to, reverse osmosis, precipitation of minerals and solids, and/or solar evaporation, or any combination therein. Exemplary aspects of each of these processes are provided below, wherein one of ordinary skill will appreciate that such aspects are not exhaustive to each process and that steps for implementing each process are generally known in the art.

With reverse osmosis, it is suggested by some that such process does not concentrate all minerals equally in the same ratio that exists in naturally occurring seawater. Some minerals exist in a higher concentration, and some trace minerals exist below detection levels. Most of the sodium chloride found in naturally occurring seawater is retained via this process, wherein no adverse egg-production effects due to the presence of sodium chloride have been noted. It is also noted that the aforementioned bioactive enzymes present in naturally occurring seawater are largely preserved through this process. For some embodiments, the reverse osmosis process may also comprise an electrolysis procedure to further refine the mineral/enzyme composition of the derived seawater concentrate as desired. Namely, because electrolysis is particularly useful in extracting select minerals from seawater, most notably extracting metals, some seawater concentrate derivations described herein have included implementing an electrolysis procedure. In a particular embodiment, such electrolysis procedure is a late stage procedure performed after reverse osmosis. Alternatively, rather than being coupled with a reverse osmosis procedure, it is contemplated that electrolysis can also be used as a stand alone process to yield a seawater concentrate with a desired mineral/enzyme composition.

With respect to precipitation, it has been discovered that such process extracts minerals, elements, and enzymes in a ratio that most closely resembles the naturally occurring ratio found in seawater, although total concentrations are significantly higher by volume due to the lesser amount of water. In some trials, this process has been observed to remove up to ninety five percent of the sodium chloride that exists in naturally occurring seawater. The lesser presence of sodium chloride, however, has not had adverse egg-production effects due to the small seawater fluid dosages administered to each chicken over the egg-laying cycle. This process also has been tested to show that bioactive enzymes exist in the final concentrate.

It has been found that solar evaporation results in the largest concentration of sodium chloride due to the fact that evaporation increases the saturation of mineral content and the sodium chloride is first to crystallize out of the solution. The balance of minerals and elements remain in the solution in the brine from which the sodium chloride separates. The crystallized precipitate does include some level of bioactivity, but this product is generally administered in greater volumes to recognize the benefit of the enzyme bioactivity.

Figure 17:
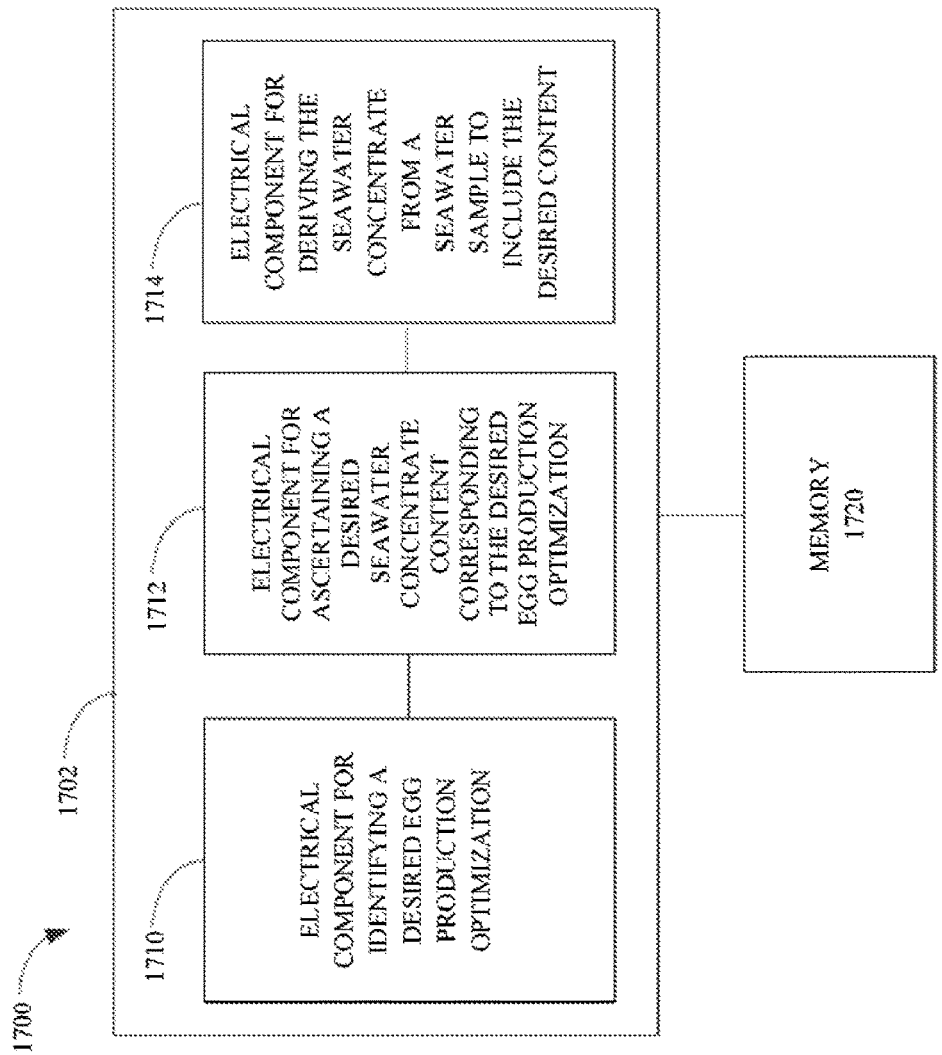
FIG. 17 illustrates another exemplary coupling of electrical components that facilitates optimizing egg production characteristics according to an embodiment.

Referring next to FIG. 17, illustrated is an exemplary system 1700 that facilitates optimizing egg production characteristics according to an embodiment. System 1700 and/or instructions for implementing system 1700 can physically reside within a computing device, for instance, wherein system 1700 includes functional blocks that can represent functions implemented by a processor using instructions and/or data from a computer readable storage medium. System 1700 includes a logical grouping 1702 of electrical components that can act in conjunction similar to logical groupings 302, 602, 902, 1202, and 1502 respectively corresponding to systems 300, 600, 900, 1200, and 1500. As illustrated, logical grouping 1702 can include an electrical component for identifying a desired egg production optimization 1710. Furthermore, logical grouping 1702 can include an electrical component for ascertaining a desired seawater concentrate content corresponding to the desired egg production optimization 1712. Logical grouping 1702 can also include an electrical component for deriving the seawater concentrate from a seawater sample to include the desired content 1714. Additionally, system 1700 can include a memory 1720 that retains instructions for executing functions associated with electrical components 1710, 1712, and 1714. While shown as being external to memory 1720, it is to be understood that electrical components 1710, 1712, and 1714 can exist within memory 1720.

Figure 18:
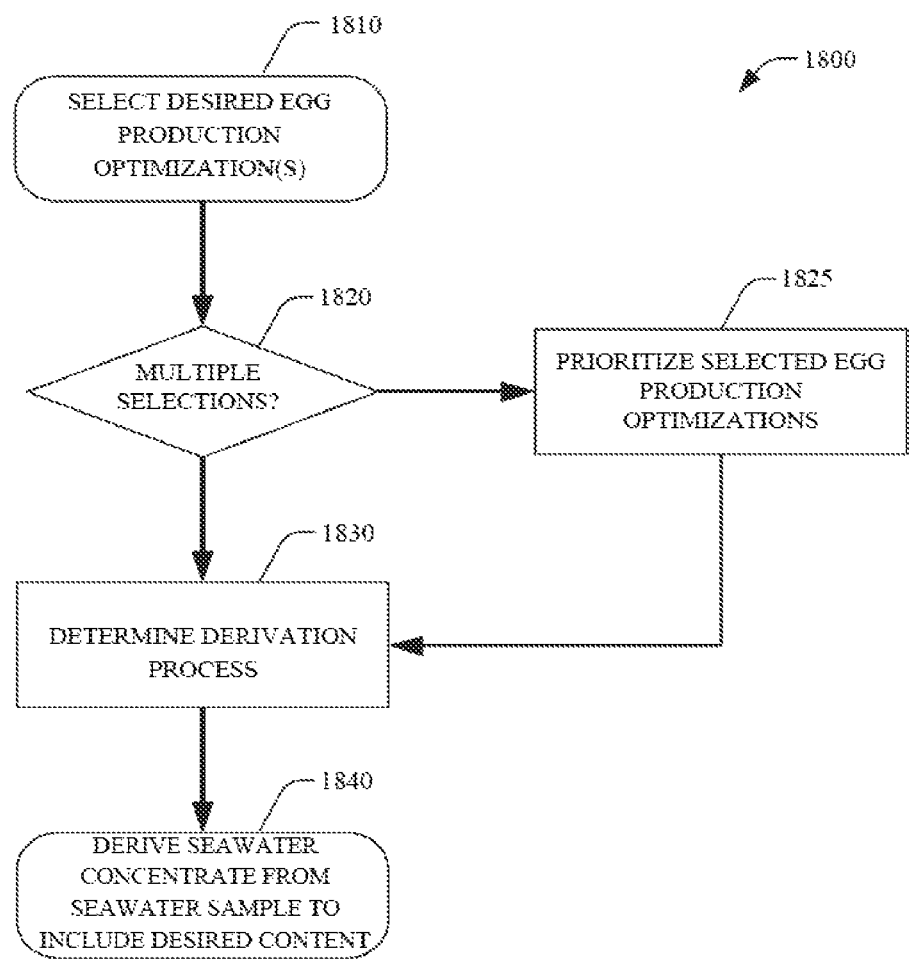
FIG. 18 illustrates a flow diagram of an exemplary methodology that facilitates optimizing egg production characteristics in accordance with an aspect of the subject specification.

Referring next to FIG. 18, a flow chart illustrating an exemplary method to facilitate optimizing egg production characteristics is provided. As illustrated, process 1800 includes a series of acts that may be performed within a computing device according to an aspect of the subject specification. For instance, process 1800 may be implemented by employing a processor to execute computer executable instructions stored on a computer readable storage medium to implement the series of acts. In another embodiment, a computer-readable storage medium comprising code for causing at least one computer to implement the acts of process 1800 are contemplated.

In an aspect, process 1800 begins with desired egg-production optimizations being selected at act 1810, wherein single and/or multiple optimizations may be selected. For this particular embodiment, process 1800 then continues to act 1820 where a determination is made as to whether multiple optimizations have been selected. If multiple optimizations are indeed selected, process 1800 proceeds to act 1825 where the selected egg-production optimizations are prioritized relative to each other. Here, any of a plurality of prioritization algorithms can be implemented. For instance, as stated previously, it is contemplated that user-based prioritization weights may be assigned to the selected optimizations, as well as default weights. User-based prioritization weights, for example, may be derived from a user's ranking of the selected optimizations and/or from a user's actual weighting of such optimizations. Alternatively, if no relative preferences are provided by a user, a default prioritization system can be implemented where the selected optimizations are generally prioritized evenly.

Once the prioritization weights are determined, or if multiple optimizations are not selected, process 1800 proceeds to act 1830 where a desired derivation process is determined. Here, it should be noted that such process may be any of a plurality of processes including, for example, reverse osmosis, precipitation, solar evaporation, and/or electrolysis, or any combination therein, as previously described. It should be further noted that particular processes may be more desirable depending on any of a plurality of factors including, for example, the selected egg-production optimization(s), various chicken/flock characteristics (e.g., age and/or breed), etc. To facilitate determining which process to select, it is contemplated that a lookup table may be utilized. Once the desired process has been determined, process 1800 then concludes at act 1850 with a seawater concentrate being derived from a seawater sample to include a desired content.

Here, it should be noted that the desired content referenced in act 1850 can vary. For instance, the desired content may include a seawater concentrate having a threshold level of at least one element. Here, it should be appreciated that such threshold level can be directed towards a threshold level of a particular mineral/element independent of other minerals/elements, and/or a threshold level of the mineral/element in proportion to other minerals/elements. Indeed, since different egg-production optimizations may be particularly sensitive to different minerals/elements, either individually or in mineral/element combinations, the threshold level of a particular mineral/element may vary depending on the corresponding egg-production optimization, as well as whether the threshold level is independent of other minerals/elements or in proportion to all/some of the other minerals/elements.

As mentioned previously, seven elements are deemed "major" based on their abundance in mammals (i.e., calcium, phosphorus, potassium, sulfur, sodium, chlorine, and magnesium). Accordingly, in one embodiment, the aforementioned threshold level corresponds to at least one of calcium, phosphorus, potassium, sulfur, sodium, chlorine, or magnesium. In another embodiment, however, the threshold level corresponds to each of a plurality of individual element threshold levels respectively corresponding to calcium, phosphorus, potassium, sulfur, sodium, chlorine, and magnesium.

As also mentioned previously, thirteen elements have been identified as being particularly important to biological processes, wherein those elements include potassium, chlorine, sodium, calcium, phosphorus, magnesium, zinc, iron, manganese, copper, iodine, selenium, and molybdenum. Accordingly, the desired content referenced in act 1850 content may include a seawater concentrate having a threshold level corresponding to at least one of potassium, chlorine, sodium, calcium, phosphorus, magnesium, zinc, iron, manganese, copper, iodine, selenium, or molybdenum. Alternatively, the threshold level may correspond to each of a plurality of individual element threshold levels respectively corresponding to potassium, chlorine, sodium, calcium, phosphorus, magnesium, zinc, iron, manganese, copper, iodine, selenium, and molybdenum.

The desired content referenced in act 1850 content may also include desired levels of bioactive enzymes. For instance, in a particular embodiment, the desired content may include a threshold level of at least one enzyme. In another embodiment, however, the desired content includes a threshold level of both at least one enzyme and at least one element.

In order to adequately preserve the contents of the disclosed seawater concentrate while in storage or transportation, particular handling protocols are contemplated. Namely, protocols for prolonging the shelf life of the seawater concentrate are contemplated, wherein the active components of the concentrate (i.e., minerals, elements, and enzymes) are preserved.

Figure 19:
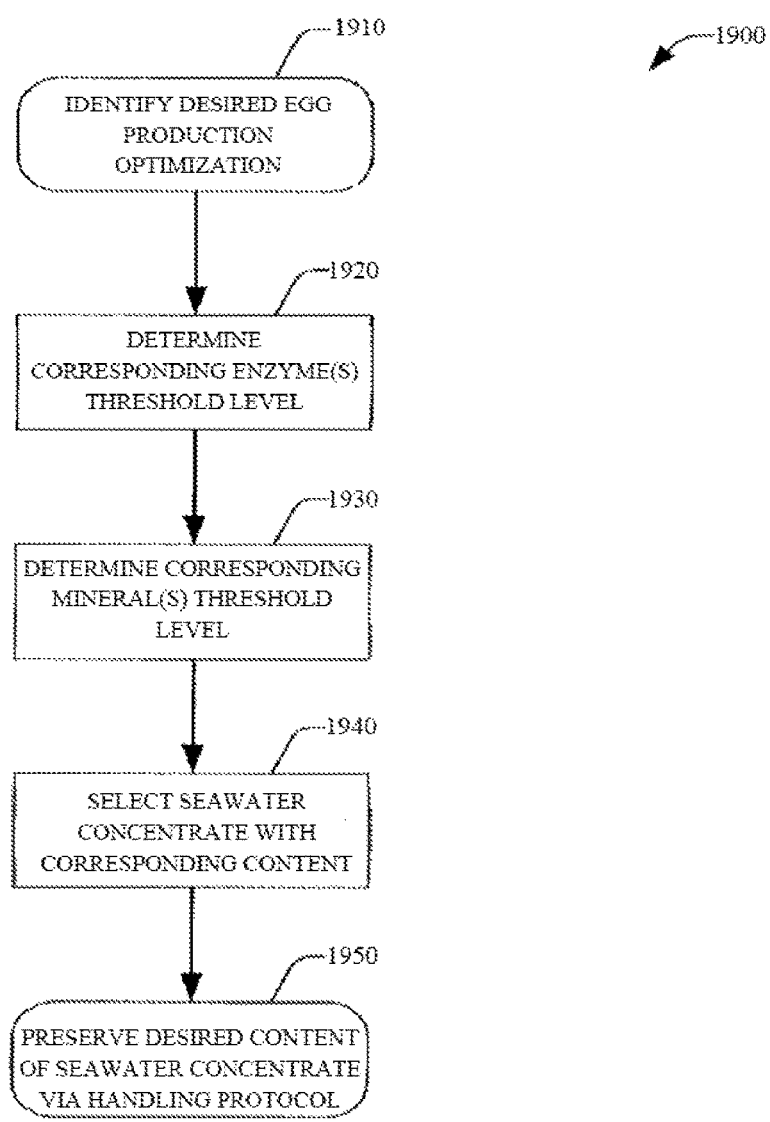
FIG. 19 illustrates a flow diagram of another exemplary methodology that facilitates optimizing egg production characteristics in accordance with an aspect of the subject specification.

Referring next to FIG. 19, a flow chart illustrating an exemplary method to facilitate optimizing egg production characteristics via a seawater concentrate handling protocol is provided. As illustrated, process 1900 includes a series of acts that may be performed within a computing device according to an aspect of the subject specification. For instance, process 1900 may be implemented by employing a processor to execute computer executable instructions stored on a computer readable storage medium to implement the series of acts. In another embodiment, a computer-readable storage medium comprising code for causing at least one computer to implement the acts of process 1900 are contemplated.

In an aspect, process 1900 begins with desired egg-production optimizations being selected at act 1910, wherein single and/or multiple optimizations may again be selected. For this particular embodiment, process 1900 then continues to act 1920 where a determination is made regarding the appropriate enzyme threshold level(s) corresponding to the desired egg-production optimizations selected at act 1910. Similarly, at act 1930, process 1900 determines the appropriate mineral/element threshold level(s) corresponding to the desired egg-production optimizations. A seawater concentrate having a content the desired enzyme, mineral, and element threshold levels is then selected at act 1940.

At act 1950, process 1900 concludes with the desired content of the seawater concentrate being preserved via an appropriate handling protocol. For instance, because light may harm enzymes in the seawater concentrate, the handling protocol may include storing the concentrate in an opaque container. It may also be desirable to properly seal a seawater concentrate container to minimize possibility of oxidation or evaporation of the concentrate.

The environment in which the seawater concentrate is stored and/or transported may also be monitored. For instance, handling protocols may include avoiding having the seawater concentrate near strong magnetic fields. The temperature at which the concentrate is stored may also be closely monitored. In a particular handling protocol, the seawater concentrate is stored at a temperature above thirty-two degrees Fahrenheit so as to avoid having the concentrate freeze. In another handling protocol, the seawater concentrate is stored at a temperature below one hundred twenty degrees Fahrenheit, since it has been found that enzyme activity is negatively affected by elevated temperatures. Namely, it has been found that enzyme degradation begins at approximately one hundred twenty degrees Fahrenheit, and that enzymes are mostly destroyed at temperatures greater than one hundred fifty degrees Fahrenheit Exemplary Networked and Distributed Environments One of ordinary skill in the art can appreciate that various embodiments for implementing the use of a computing device and related embodiments described herein can be implemented in connection with any computer or other client or server device, which can be deployed as part of a computer network or in a distributed computing environment, and can be connected to any kind of data store. Moreover, one of ordinary skill in the art will appreciate that such embodiments can be implemented in any computer system or environment having any number of memory or storage units, and any number of applications and processes occurring across any number of storage units. This includes, but is not limited to, an environment with server computers and client computers deployed in a network environment or a distributed computing environment, having remote or local storage.

Figure 20:
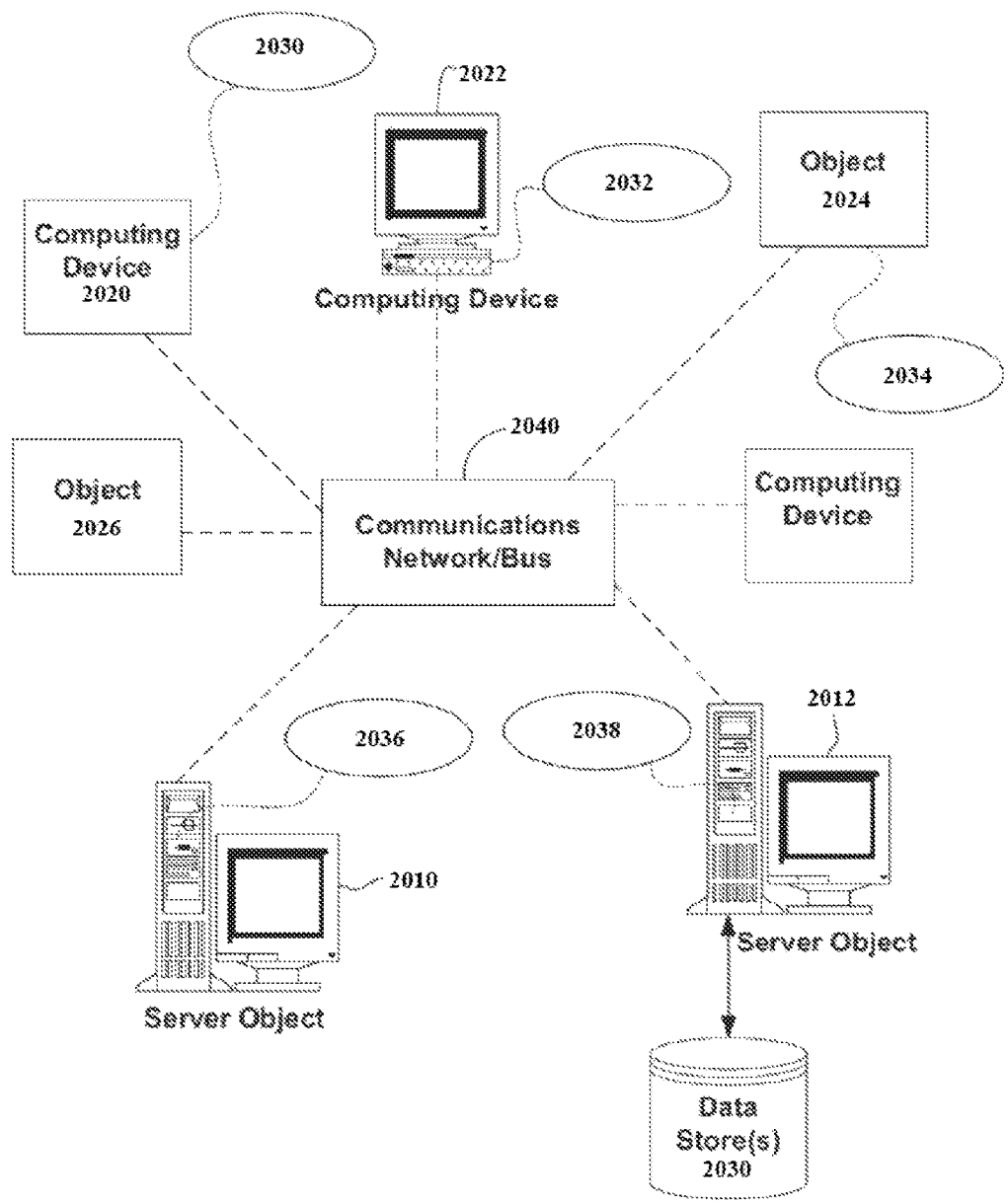
FIG. 20 is a block diagram representing exemplary non-limiting networked environments in which various embodiments described herein can be implemented.

FIG. 20 provides a non-limiting schematic diagram of an exemplary networked or distributed computing environment. The distributed computing environment comprises computing objects or devices 2010, 2012, etc. and computing objects or devices 2020, 2022, 2024, 2026, 2028, etc., which may include programs, methods, data stores, programmable logic, etc., as represented by applications 2030, 2032, 2034, 2036, 2038. It can be appreciated that computing objects or devices 2010, 2012, etc. and computing objects or devices 2020, 2022, 2024, 2026, 2028, etc. may comprise different devices, such as PDAs (personal digital assistants), audio/video devices, mobile phones, MP3 players, laptops, etc.

Each computing object or device 2010, 2012, etc. and computing objects or devices 2020, 2022, 2024, 2026, 2028, etc. can communicate with one or more other computing objects or devices 2010, 2012, etc. and computing objects or devices 2020, 2022, 2024, 2026, 2028, etc. by way of the communications network 2040, either directly or indirectly. Even though illustrated as a single element in FIG. 20, network 2040 may comprise other computing objects and computing devices that provide services to the system of FIG. 20, and/or may represent multiple interconnected networks, which are not shown. Each computing object or device 2010, 2012, etc. or 2020, 2022, 2024, 2026, 2028, etc. can also contain an application, such as applications 2030, 2032, 2034, 2036, 2038, that might make use of an API (application programming interface), or other object, software, firmware and/or hardware, suitable for communication with or implementation of the aspects described herein.

There are a variety of systems, components, and network configurations that support distributed computing environments. For example, computing systems can be connected together by wired or wireless systems, by local networks or widely distributed networks. Currently, many networks are coupled to the Internet, which provides an infrastructure for widely distributed computing and encompasses many different networks, though any network infrastructure can be used for exemplary communications made incident to the techniques as described in various embodiments.

Thus, a host of network topologies and network infrastructures, such as client/server, peer-to-peer, or hybrid architectures, can be utilized. In a client/server architecture, particularly a networked system, a client is usually a computer that accesses shared network resources provided by another computer, e.g., a server. In the illustration of FIG. 20, as a non-limiting example, computing objects or devices 2020, 2022, 2024, 2026, 2028, etc. can be thought of as clients and computing objects or devices 2010, 2012, etc. can be thought of as servers where computing objects or devices 2010, 2012, etc. provide data services, such as receiving data from computing objects or devices 2020, 2022, 2024, 2026, 2028, etc., storing of data, processing of data, transmitting data to computing objects or devices 2020, 2022, 2024, 2026, 2028, etc., although any computer can be considered a client, a server, or both, depending on the circumstances. Any of these computing devices may be processing data, or requesting services or tasks that may implicate an infrastructure for optimizing egg production characteristics and related techniques as described herein for one or more embodiments.

A server is typically a remote computer system accessible over a remote or local network, such as the Internet or wireless network infrastructures. The client process may be active in a first computer system, and the server process may be active in a second computer system, communicating with one another over a communications medium, thus providing distributed functionality and allowing multiple clients to take advantage of the information-gathering capabilities of the server. Any software objects utilized pursuant to the user profiling can be provided standalone, or distributed across multiple computing devices or objects.

In a network environment in which the communications network/bus 2040 is the Internet, for example, the computing objects or devices 2010, 2012, etc. can be Web servers with which the computing objects or devices 2020, 2022, 2024, 2026, 2028, etc. communicate via any of a number of known protocols, such as HTTP. As mentioned, computing objects or devices 2010, 2012, etc. may also serve as computing objects or devices 2020, 2022, 2024, 2026, 2028, etc., or vice versa, as may be characteristic of a distributed computing environment.

Exemplary Computing Device

As mentioned, various of the aforementioned embodiments apply to any device wherein it may be desirable to include a computing device to optimize egg production characteristics according to the aspects disclosed herein. It is understood, therefore, that handheld, portable and other computing devices and computing objects of all kinds are contemplated for use in connection with the various embodiments described herein, i.e., anywhere that a device may provide some functionality in connection with utilizing a seawater solution to optimize egg production characteristics. Accordingly, the below general purpose remote computer described below in FIG. 21 is but one example, and the embodiments of the subject disclosure may be implemented with any client having network/bus interoperability and interaction.

Although not required, any of the embodiments can partly be implemented via an operating system, for use by a developer of services for a device or object, and/or included within application software that operates in connection with the operable component(s). Software may be described in the general context of computer executable instructions, such as program modules, being executed by one or more computers, such as client workstations, servers or other devices. Those skilled in the art will appreciate that network interactions may be practiced with a variety of computer system configurations and protocols.

Figure 21:
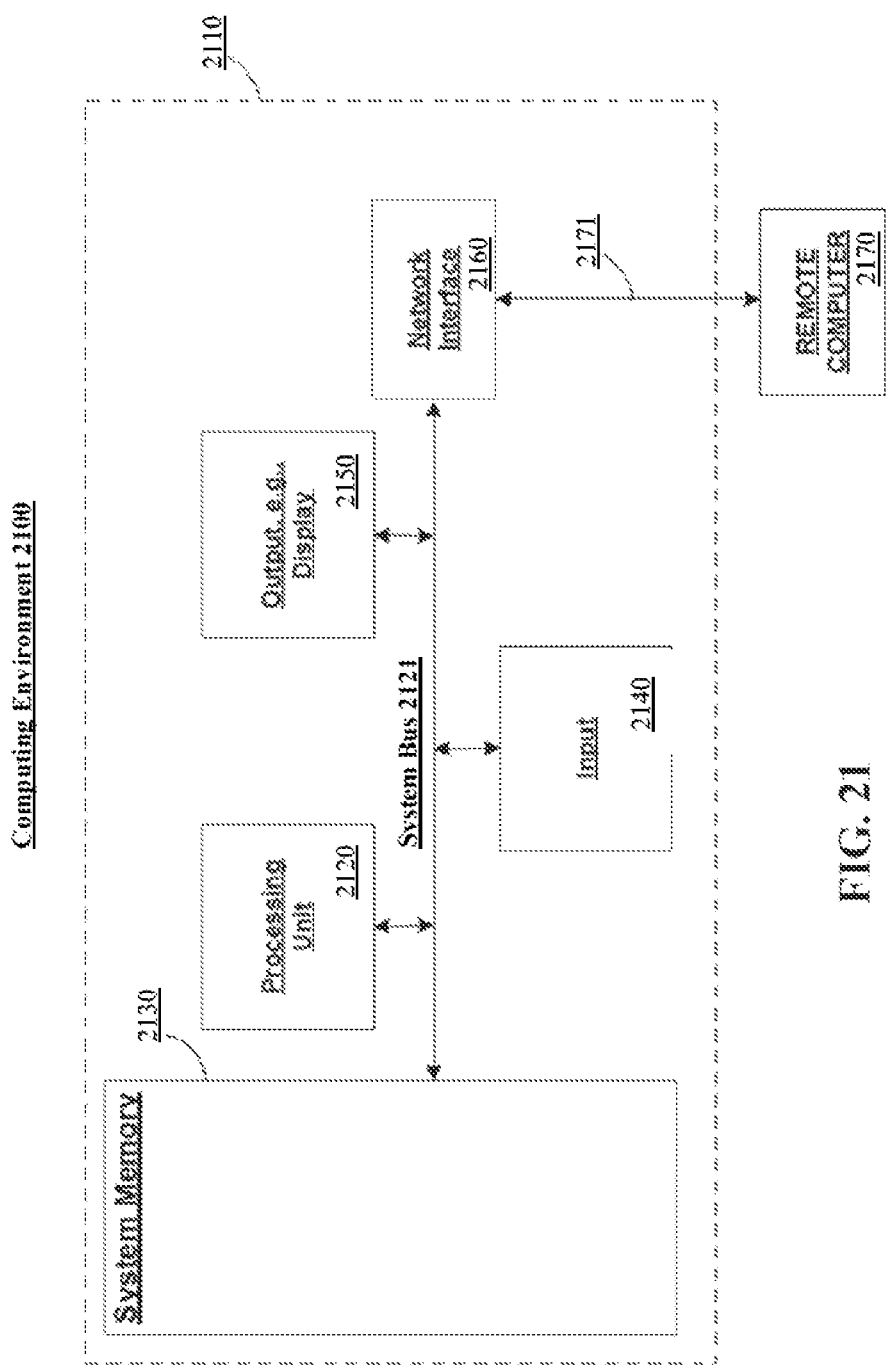
FIG. 21 is a block diagram representing an exemplary non-limiting computing system or operating environment in which one or more aspects of various embodiments described herein can be implemented.

FIG. 21 thus illustrates an example of a suitable computing system environment 2100 in which one or more of the embodiments may be implemented, although as made clear above, the computing system environment 2100 is only one example of a suitable computing environment and is not intended to suggest any limitation as to the scope of use or functionality of any of the embodiments. The computing environment 2100 is not to be interpreted as having any dependency or requirement relating to any one or combination of components illustrated in the exemplary operating environment 2100.

With reference to FIG. 21, an exemplary remote device for implementing one or more embodiments herein can include a general purpose computing device in the form of a handheld computer 2110. Components of handheld computer 2110 may include, but are not limited to, a processing unit 2120, a system memory 2130, and a system bus 2121 that couples various system components including the system memory to the processing unit 2120.

Computer 2110 typically includes a variety of computer readable media and can be any available media that can be accessed by computer 2110. The system memory 2130 may include computer storage media in the form of volatile and/or nonvolatile memory such as read only memory (ROM) and/or random access memory (RAM). By way of example, and not limitation, memory 2130 may also include an operating system, application programs, other program modules, and program data.

A user may enter commands and information into the computer 2110 through input devices 2140 A monitor or other type of display device is also connected to the system bus 2121 via an interface, such as output interface 2150. In addition to a monitor, computers may also include other peripheral output devices such as speakers and a printer, which may be connected through output interface 2150.

The computer 2110 may operate in a networked or distributed environment using logical connections to one or more other remote computers, such as remote computer 2170. The remote computer 2170 may be a personal computer, a server, a router, a network PC, a peer device or other common network node, or any other remote media consumption or transmission device, and may include any or all of the elements described above relative to the computer 2110. The logical connections depicted in FIG. 21 include a network 2171, such local area network (LAN) or a wide area network (WAN), but may also include other networks/buses. Such networking environments are commonplace in homes, offices, enterprise-wide computer networks, intranets and the Internet.

As mentioned above, while exemplary embodiments have been described in connection with various computing devices, networks and advertising architectures, the underlying concepts may be applied to any network system and any computing device or system in which it is desirable to publish, build applications for or consume data in connection with interactions with a cloud or network service.

There are multiple ways of implementing one or more of the embodiments described herein, e.g., an appropriate API, tool kit, driver code, operating system, control, standalone or downloadable software object, etc. which enables applications and services to implement the aspects described herein. Embodiments may be contemplated from the standpoint of an API (or other software object), as well as from a software or hardware object that facilitates optimizing egg production characteristics in accordance with one or more of the described embodiments. Various implementations and embodiments described herein may have aspects that are wholly in hardware, partly in hardware and partly in software, as well as in software.

The word "exemplary" is used herein to mean serving as an example, instance, or illustration. For the avoidance of doubt, the subject matter disclosed herein is not limited by such examples. In addition, any aspect or design described herein as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, for the avoidance of doubt, such terms are intended to be inclusive in a manner similar to the term "comprising" as an open transition word without precluding any additional or other elements.

As mentioned, the various techniques described herein may be implemented in connection with hardware or software or, where appropriate, with a combination of both. As used herein, the terms "component," "system" and the like are likewise intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on computer and the computer can be a component. One or more components may reside within a process and/or thread of execution and a component may be localized on one computer and/or distributed between two or more computers.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it is noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

In view of the exemplary systems described supra, methodologies that may be implemented in accordance with the disclosed subject matter can be appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Where non-sequential, or branched, flow is illustrated via flowchart, it can be appreciated that various other branches, flow paths, and orders of the blocks, may be implemented which achieve the same or a similar result. Moreover, not all illustrated blocks may be required to implement the methodologies described hereinafter.

While in some embodiments, a client side perspective is illustrated, it is to be understood for the avoidance of doubt that a corresponding server perspective exists, or vice versa. Similarly, where a method is practiced, a corresponding device can be provided having storage and at least one processor configured to practice that method via one or more components.

While the various embodiments have been described in connection with the preferred embodiments of the various figures, it is to be understood that other similar embodiments may be used or modifications and additions may be made to the described embodiment for performing the same function without deviating there from. Still further, one or more aspects of the above described embodiments may be implemented in or across a plurality of processing chips or devices, and storage may similarly be affected across a plurality of devices. Therefore, the present invention should not be limited to any single embodiment, but rather should be construed in breadth and scope in accordance with the appended claims.

What is claimed is:

1. A method comprising:
   identifying an optimized egg production characteristic of hens;
   ascertaining a desired content of a seawater concentrate that produces the optimized egg production characteristic when fed to hens in a trial;
   deriving the seawater concentrate from a seawater sample to include the desired content; and
   feeding a hen the seawater concentrate of the desired content to produce an egg having the optimized egg production characteristic.

2. The method of claim 1, the deriving performed via at least one of a reverse osmosis process, a precipitation process, a solar evaporation process, and an electrolysis process.

3. The method of claim 1, the desired content including a threshold level of at least one element.

4. The method of claim 3, the threshold level corresponding to at least one of calcium, phosphorus, potassium, sulfur, sodium, chlorine, and magnesium.

5. The method of claim 3, the threshold level corresponding to each of a plurality of individual element threshold levels, the plurality of individual element threshold levels respectively corresponding to calcium, phosphorus, potassium, sulfur, sodium, chlorine, and magnesium.

6. The method of claim 3, the threshold level corresponding to at least one of potassium, chlorine, sodium, calcium, phosphorus, magnesium, zinc, iron, manganese, copper, iodine, selenium, and molybdenum.

7. The method of claim 3, the threshold level corresponding to each of a plurality of individual element threshold levels, the plurality of individual element threshold levels respectively corresponding to potassium, chlorine, sodium, calcium, phosphorus, magnesium, zinc, iron, manganese, copper, iodine, selenium, and molybdenum.

8. The method of claim 3, the threshold level corresponding to each of a plurality of individual element threshold levels, the plurality of individual element threshold levels respectively corresponding to potassium, chlorine, sodium, calcium, phosphorus, magnesium, zinc, iron, manganese, copper, iodine, selenium, and molybdenum.

9. The method of claim 1, the desired content including a threshold level of at least one enzyme.

10. The method of claim 1, the desired content including a threshold level of at least one enzyme.

11. A method, comprising:
    identifying an optimized egg production characteristic of hens;
    ascertaining a desired content of a seawater concentrate that produces the optimized egg production characteristic when fed to hens in a trial;
    deriving the seawater concentrate from a seawater sample to include the desired content;
    selecting a customized ratio of the seawater concentrate and a non-seawater fluid that produces the optimized egg production characteristic when fed to hens in the trial; and
    feeding a hen the customized ratio of the seawater concentrate of the desired content and the non-seawater fluid to produce an egg having the optimized egg production characteristic.

12. The method of claim 11, the deriving performed via at least one of a reverse osmosis process, a precipitation process, a solar evaporation process, and an electrolysis process.

13. The method of claim 11, the desired content including a threshold level of at least one element.

14. The method of claim 13, the threshold level corresponding to at least one of calcium, phosphorus, potassium, sulfur, sodium, chlorine, and magnesium.

15. The method of claim 13, the threshold level corresponding to each of a plurality of individual element threshold levels, the plurality of individual element threshold levels respectively corresponding to calcium, phosphorus, potassium, sulfur, sodium, chlorine, and magnesium.

16. The method of claim 13, the threshold level corresponding to at least one of potassium, chlorine, sodium, calcium, phosphorus, magnesium, zinc, iron, manganese, copper, iodine, selenium, and molybdenum.

17. A method, comprising:
    identifying an optimized egg production characteristic of hens from a plurality of egg production characteristics including robustness, egg shell thickness, and size;
    ascertaining a desired content of a seawater concentrate that produces the optimized egg production characteristic when fed to hens in a trial;
    deriving the seawater concentrate from a seawater sample to include the desired content;
    selecting a customized ratio of the seawater concentrate and a non-seawater fluid that produces the optimized egg production characteristic when fed to hens in the trial; and
    feeding a hen the customized ratio of the seawater concentrate of the desired content and the non-seawater fluid to produce an egg having the optimized egg production characteristic.

18. The method of claim 17, the deriving performed via at least one of a reverse osmosis process, a precipitation process, a solar evaporation process, and an electrolysis process.

19. The method of claim 17, the desired content including a threshold level of at least one element.

20. The method of claim 17, the desired content including a threshold level of at least one enzyme.

* * * * *